(12) United States Patent
Fukita et al.

(10) Patent No.: US 10,562,800 B2
(45) Date of Patent: Feb. 18, 2020

(54) METHOD FOR PROCESSING FLUORINE-CONTAINING AQUEOUS SOLUTION

(71) Applicant: DAIKIN INDUSTRIES, LTD., Osaka-shi, Osaka (JP)

(72) Inventors: Nobuo Fukita, Settsu (JP); Shoji Itakura, Settsu (JP); Michinobu Koizumi, Settsu (JP); Kenji Otoi, Settsu (JP); Hitoshi Motoyama, Settsu (JP); Kayui Go, Settsu (JP)

(73) Assignee: DAIKIN INDUSTRIES, LTD., Osaka-Shi (JP)

( * ) Notice: Subject to any disclaimer, the term of this patent is extended or adjusted under 35 U.S.C. 154(b) by 382 days.

(21) Appl. No.: 15/300,651

(22) PCT Filed: Mar. 31, 2015

(86) PCT No.: PCT/JP2015/060163
§ 371 (c)(1),
(2) Date: Sep. 29, 2016

(87) PCT Pub. No.: WO2015/152258
PCT Pub. Date: Oct. 8, 2015

(65) Prior Publication Data
US 2017/0113953 A1  Apr. 27, 2017

(30) Foreign Application Priority Data

Mar. 31, 2014  (JP) .................................. 2014-073353

(51) Int. Cl.
*C02F 1/68* (2006.01)
*B01F 3/08* (2006.01)
(Continued)

(52) U.S. Cl.
CPC ............ *C02F 1/683* (2013.01); *B01F 3/0865* (2013.01); *B01F 3/0873* (2013.01);
(Continued)

(58) Field of Classification Search
None
See application file for complete search history.

(56) References Cited

U.S. PATENT DOCUMENTS 4,828,712 A * 5/1989 Reynolds .................. C02F 1/26
  210/688
5,122,356 A * 6/1992 Kawamura ........... C01B 7/0706
  423/488

FOREIGN PATENT DOCUMENTS

JP  1-44392 B2  9/1989
JP  5-27564 B2  4/1993

OTHER PUBLICATIONS

Steffen's Chemistry Pages, "Density of hydrochloric acid", pp. 1-2, accessed online Nov. 14, 2018. (Year: 2018).*
(Continued)

*Primary Examiner* — Clare M Perrin
(74) *Attorney, Agent, or Firm* — Birch, Stewart, Kolasch & Birch LLP

(57) ABSTRACT

The present disclosure provides a method for processing a fluorine-containing aqueous solution. The method comprises a reaction step for mixing in a vertical direction the fluorine-containing aqueous solution and a disiloxane compound represented by a general formula $R_a R_b R_c SiOSiR_d R_e R_f$, wherein $R_a$, $R_b$, $R_c$, $R_d$, $R_e$ and $R_f$ are selected independently from each other from a group consisting of a phenyl group and an alkyl group comprising from 1 to 20 carbon atoms and hydrogen, to react a fluorine ion in the fluorine-containing aqueous solution with the disiloxane compound, obtaining a first reaction liquid containing a monofluorosi-
(Continued)

lane compound represented by general formulas $R_aR_bR_cSiF$ and $R_dR_eR_fSiF$.

75 Claims, 12 Drawing Sheets

(51) Int. Cl.
    *C02F 1/36*      (2006.01)
    *B01F 5/02*      (2006.01)
    *B01F 5/10*      (2006.01)
    *C02F 103/34*      (2006.01)
    *C02F 101/14*      (2006.01)

(52) U.S. Cl.
    CPC .............. *B01F 5/0212* (2013.01); *C02F 1/36* (2013.01); *B01F 2215/0036* (2013.01); *C02F 2101/14* (2013.01); *C02F 2103/34* (2013.01); *C02F 2301/046* (2013.01)

(56) References Cited

OTHER PUBLICATIONS

"Shin kougaiboushi no gijutsu to houki 2013 suishitsu hen (New technique and regulations of pollution prevention 2013 Water quality edition)" written and edited by Editorial committee of Technique and regulations of pollution prevention, Japan Environment Management Association for Industry, Jan. 2013, pp. 468-469 (with English-Language Translation).
Translated International Preliminary Report on Patentability issued in International Application No. PCT/JP2015/060163 dated Oct. 4, 2016.

* cited by examiner

METHOD FOR PROCESSING FLUORINE-CONTAINING AQUEOUS SOLUTION

TECHNICAL FIELD

The present invention relates to a method for processing a fluorine-containing aqueous solution and an apparatus for processing a fluorine-containing aqueous solution.

BACKGROUND ART

In recent years, along with strengthened environmental regulations concerning fluorine, there is an increased need for a method for removing fluorine from waste liquid generated in manufacturing process of fluorine compound such as hydrochloric acid and sulfuric acid containing fluorine.

Conventionally, as a method for removing fluorine in an aqueous solution, a method of adding calcium to a fluorine-containing aqueous solution and adjusting pH of the aqueous solution to neutral to precipitate calcium fluoride is known (Non Patent Literature 1). However, when fluorine in an acidic aqueous solution is removed by this method, for example, the aqueous solution after removal of fluorine becomes neutral. Therefore, it is impossible to reuse the acidic aqueous solution after removal of fluorine.

On the other hand, Patent Literature 1 describes a method for purifying hydrochloric acid comprising: a step for bringing a silicon compound such as trimethylchlorosilane into contact with the hydrochloric acid containing hydrogen fluoride; and a step for recovering trialkylfluorosilane compound formed in the contacting step. In this method, the recovery step consists of a step for hydrolyzing the trialkylfluorosilane compound to convert it into a trialkylsilanol compound and a step for condensing the trialkylsilanol compound to convert it into a hexaalkyl disiloxane compound. The hexaalkyl disiloxane compound obtained in the recovery step is chlorinated to form trialkylchlorosilane compound, and the trialkylchlorosilane compound is reused in the contacting step. Hydrochloric acid having higher concentration of more than 25% by weight is required to chlorinate the hexaalkyl disiloxane compound.

Patent Literature 2 describes a method for processing a fluorine-containing waste liquid, characterized by filling the fluorine-containing waste liquid with a solid adsorbent on which hexaalkyl disiloxane is supported, blowing an air into the waste liquid while maintaining the waste liquid in an acidic state, guiding a fluorotrialkylsilane scattered from the waste liquid into an absorption vessel receiving an alkali solution and a solid adsorbent, forming a trialkylsilanol and a fluorine ion in the absorption vessel, and recovering the fluorine ion in the alkali solution while adsorbing the trialkylsilanol as a hexaalkyl disiloxane on the solid adsorbent. This method requires as long as three hours to remove fluorine from the fluorine-containing waste liquid. Further, since this method requires the handling of the solid adsorbent and fluorotrialkylsilane scattered with the air in addition to the fluorine-containing waste liquid and hexaalkyl disiloxane which are liquid, the processing in this method is cumbersome and can bring about high cost.

PRIOR ART LITERATURE

Patent Literature

Patent Literature 1: JP H05-27564 B2
Patent Literature 2: JP H01-44392 B2

Non Patent Literature

Non Patent Literature 1: "Shin kougaiboushi no gijutsu to houki 2013 suishitsu hen (New technique and regulations of pollution prevention 2013 Water quality edition)" written and edited by Editorial committee of Technique and regulations of pollution prevention, Japan Environmental Management Association for Industry, January 2013, p. 468-469

SUMMARY OF INVENTION

Technical Problem

In the purification method described in Patent Literature 1, a reaction of hydrochloric acid containing hydrogen fluoride with trialkylchlorosilane in the contacting step to obtain trialkylfluorosilane is represented by the following formula (i):

$$R^1R^2R^3SiCl + HF \rightarrow R^1R^2R^3SiF + HCl \qquad (i)$$

wherein $R^1$, $R^2$ and $R^3$ represent the same or different alkyl group having 1 to 4 carbon atoms, respectively. Fluorine ion is removed from the hydrochloric acid by this reaction.

Then, the trialkylfluorosilane formed by the reaction of the formula (i) is recovered, and the trialkylfluorosilane is regenerated into the trialkylchlorosilane by reactions represented by the following formulas (ii) to (iv). First, the recovered trialkylfluorosilane is hydrolyzed by the reaction represented by the following formula (ii) under neutral or basic condition.

$$R^1R^2R^3SiF + OH^- \rightarrow R^1R^2R^3SiOH + F^- \qquad (ii)$$

A trialkylsilanol obtained by the hydrolysis is condensed by the reaction represented by the following formula (iii) to obtain a hexaalkyl disiloxane.

$$2R^1R^2R^3SiOH \rightarrow R^1R^2R^3SiOSiR^1R^2R^3 + H_2O \qquad (iii)$$

The obtained hexaalkyl disiloxane is chlorinated by the reaction represented by the following formula (iv) to obtain a trimethylchlorosilane.

$$R^1R^2R^3SiOSiR^1R^2R^3 + 2HCl \rightarrow 2R^1R^2R^3SiCl + H_2O \qquad (iv)$$

The trialkylchlorosilane regenerated in this manner can be reused in the above-described contacting step.

The trialkylchlorosilane such as trimethylchlorosilane (hereinafter, also referred to as TMCS) used in the method described in Patent Literature 1 is known as an unstable and easily-hydrolyzable substance. Therefore, the method described in Patent Literature 1 has a problem that it is difficult to handle the trialkylchlorosilane. In particular, the reaction of the formula (iv) requires to be conducted in non-aqueous system or requires an additional treatment such as removal of the formed water with dehydrating agent in order to suppress the hydrolysis of the formed trialkylchlorosilane. Furthermore, it is necessary to use a hydrochloric acid having high concentration of more than 25% by weight to proceed with the reaction of the formula (iv), which results in an increase in cost.

The present inventors have focused their attention on a fact that it is possible to purify the fluorine-containing aqueous solution without passing through the reaction (iv), the reaction (iv) requiring the use of hydrochloric acid having high concentration, by use of a disiloxane compound represented by a general formula $R_aR_bR_cSiOSiR_dR_eR_f$ wherein Ra, Rb, Rc, Rd and Re and Rf are selected independently from each other from a group consisting of a phenyl group an alkyl group having 1 to 20 carbons and hydrogen (hereinafter, also referred to as simply "disiloxane compound") instead of trialkylchlorosilane such as TMCS.

Purification of the fluorine-containing aqueous solution by use of the disiloxane compound can be carried out by reactions represented by the following formulas (I), (II) and (III-1) to (III-3). First, a fluorine ion in the aqueous solution is reacted with the disiloxane compound by the reaction represented by the formula (I) to form monofluorosilane compounds represented by general formulas $R_aR_bR_cSiF$ and $R_dR_eR_fSiF$.

$$R_aR_bR_cSiOSiR_dR_eR_f+2H^++2F^-\rightarrow R_aR_bR_cSiF+R_dR_eR_fSiF+H_2O \quad (I)$$

The monofluorosilane compounds formed by this reaction can be easily separated from the aqueous solution since the monofluorosilane compounds are insoluble in water. As a result, a purified aqueous solution having reduced fluorine concentration compared to that before the reaction is obtained.

Then, the monofluorosilane compounds formed by the reaction of the formula (I) are regenerated into the disiloxane compound by the reactions represented by the following formulas (II) and (III-1) to (III-3).

First, the resulting monofluorosilane compounds are hydrolyzed by the reaction represented by the following formula (II) under a basic condition to form silanol compounds.

$$R_aR_bR_cSiF+R_dR_eR_fSiF+2OH^-\rightarrow R_aR_bR_cSiOH+R_dR_eR_fSiOH+2F^- \quad (II)$$

The resulting silanol compounds are dehydrated and condensed by the reactions represented by the following formulas (III-1) to (III-3) to form the disiloxane compounds.

$$2R_aR_bR_cSiOH\rightarrow(R_aR_bR_cSi)_2O+H_2O \quad (III-1)$$

$$2R_dR_eR_fSiOH\rightarrow(R_dR_eR_fSi)_2O+H_2O \quad (III-2)$$

$$R_aR_bR_cSiOH+R_dR_eR_fSiOH\rightarrow R_aR_bR_cSiOHSiR_dR_eR_f+H_2O \quad (III-3)$$

The disiloxane compounds regenerated in this manner can be recycled in the reaction of the formula (I). The regenerated disiloxane compounds may be of the same type as the original disiloxane compound, or of different type from the original disiloxane compound, or a mixture of a multiple types of disiloxane compounds.

However, the disiloxane compounds are immiscible with the fluorine-containing aqueous solution and phase-separated from the fluorine-containing aqueous solution since the disiloxane compounds are insoluble in water. Therefore, the reaction of the fluorine ion in the fluorine-containing aqueous solution with the disiloxane compound represented by the formula (I) can proceed only at an interface between an organic phase containing the disiloxane compound and an aqueous phase containing the fluorine-containing aqueous solution. Furthermore, since the disiloxane compound is a stable compound, the reaction rate of the formula (I) is slower than the reaction of the formula (i) of the trialkylchlorosilane with the fluorine ion, and it takes a long time for the reaction of the formula (I). Therefore, it is difficult to efficiently process a large amount of fluorine-containing waste liquid generated in the manufacturing process of fluorine compound by use of the disiloxane compound.

An object of the present invention is to provide a method for efficiently processing a fluorine-containing aqueous solution which can proceed with the reaction of the fluorine ion in the fluorine-containing aqueous solution with the disiloxane compound in a short time.

Solution to Problem

The present inventors have found that mixing of the fluorine-containing aqueous solution and the disiloxane compound in a vertical direction can increase drastically an opportunity of a contact between the fluorine ion and the disiloxane compound, and can efficiently proceed with the reaction of the fluorine ion in the fluorine-containing aqueous solution with the disiloxane compound in a short time. Thus, the present inventors have completed the present invention.

According to a first aspect of the present invention, there is provided a method for processing a fluorine-containing aqueous solution comprising:

a reaction step for mixing in a vertical direction a fluorine-containing aqueous solution and a disiloxane compound represented by a general formula $R_aR_bR_cSiOSiR_dR_eR_f$, wherein $R_a$, $R_b$, $R_c$, $R_d$, $R_e$ and $R_f$ are selected independently from each other from a group consisting of a phenyl group and an alkyl group comprising from 1 to 20 carbon atoms and hydrogen, to react a fluorine ion in the fluorine-containing aqueous solution with the disiloxane compound, obtaining a first reaction liquid comprising monofluorosilane compounds represented by general formulas $R_aR_bR_cSiF$ and $R_dR_eR_fSiF$.

According to a second aspect of the present invention, there is provided an apparatus for processing a fluorine-containing aqueous solution, the apparatus comprising a first reaction vessel for mixing a fluorine-containing aqueous solution and a disiloxane compound to react a fluorine ion in the fluorine-containing aqueous solution with the disiloxane compound, obtaining a first reaction liquid containing a monofluorosilane compound, wherein the first reaction vessel comprises a conduit for ejecting a liquid taken out from the first reaction vessel in the first reaction vessel, and wherein a first ejection member comprising a first nozzle is attached to a tip of the conduit.

According to a third aspect of the present invention, there is provided an apparatus for processing a fluorine-containing aqueous solution, the apparatus comprising:

a first tubular reactor for mixing a fluorine-containing aqueous solution and a disiloxane compound to react a fluorine ion in the fluorine-containing aqueous solution with the disiloxane compound, obtaining a first reaction liquid containing a monofluorosilane compound, wherein an irradiation with an ultrasonic wave is conducted by a vibrator arranged below the first tubular reactor along a flow direction in the first tubular reactor.

According to a fourth aspect of the present invention, there is provided an apparatus for processing a fluorine-containing aqueous solution, the apparatus comprising:

a first countercurrent reaction column, wherein a fluorine-containing aqueous solution is fed to an upper part of the first countercurrent reaction column, while a disiloxane compound is fed to a lower part of the first countercurrent reaction column, and wherein an organic phase comprising a disiloxane compound and a monofluorosilane compound is obtained at a top of the first countercurrent reaction column, while a purified aqueous solution with reduced fluorine concentration compared to the fluorine-containing aqueous solution is obtained at a bottom of the first countercurrent reaction column.

Advantageous Effects of Invention

According to the present invention, there is provided an efficient method for processing a fluorine-containing aqueous solution and an apparatus which can proceed with the reaction of the fluorine ion in the fluorine-containing aqueous solution and a disiloxane compound in a short time.

DESCRIPTION OF EMBODIMENTS

Figure 1:
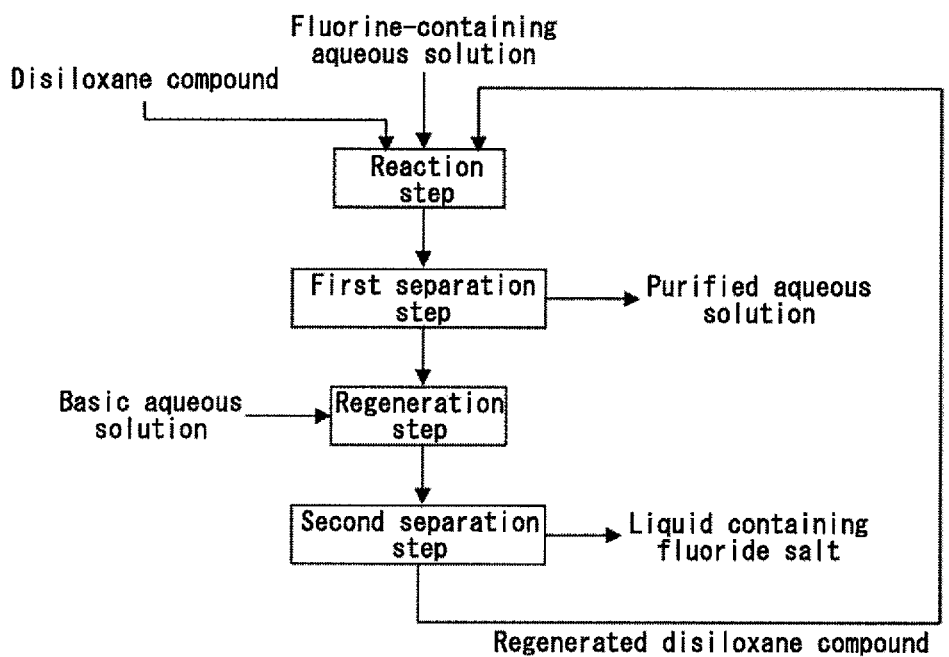
FIG. 1 is a flow chart of a method according to an embodiment of the present invention.

Hereinafter, a method for processing a fluorine-containing aqueous solution according to an embodiment of the present invention will be described with reference to the drawings. The embodiments described below and the embodiments shown in the drawings are merely an example, and the present invention is not limited to these embodiments.

FIG. 1 is a flow chart of a method for processing a fluorine-containing aqueous solution according to an embodiment of the present invention. The method according to an embodiment of the present invention comprises a reaction step. The method according to an embodiment of the present invention may further comprise a first separation step, a regeneration step and a second separation step.

[Reaction Step]

The reaction step is a step for reacting a fluorine ion in a fluorine-containing aqueous solution with a disiloxane compound to obtain a first reaction liquid containing a monofluorosilane compound. The fluorine-containing aqueous solution which can be processed by the method according to an embodiment of the present invention is not particularly limited, and the method can process various aqueous solutions containing one or more of a fluorine ion ($F^-$) and a fluorine-containing ion such as $SiF_6^{2-}$, $BF_4^-$, $PF_6^-$ and $SO_3F^-$, for example, an aqueous solution containing one or more of HF, $H_2SiF_6$, $HBF_4$, $HPF_6$ and $HSO_3F$. The method according to an embodiment of the present invention can process a fluorine-containing aqueous solution having a fluorine concentration of about 100 to 50,000 ppm to reduce the fluorine concentration in the aqueous solution to about 1 to 100 ppm. In the present specification, "fluorine concentration" means a weight concentration of the fluorine ion and the fluorine in a liquid of interest. For example, the fluorine concentration of 1,000 ppm means a concentration at which 1 g of the fluorine ion and the fluorine is present in 1 kg of the fluorine-containing aqueous solution.

The disiloxane compound which can be used in an embodiment of the present invention is a compound represented by a general formula $R_aR_bR_cSiOSiR_dR_eR_f$, wherein $R_a$, $R_b$, $R_c$, $R_d$, $R_e$ and $R_f$ are selected independently from each other from a group consisting of a phenyl group and an alkyl group comprising from 1 to 20 carbon atoms and hydrogen. Specifically, it is possible to use disiloxane ($H_3SiOSiH_3$), hexamethyl disiloxane (($H_3C)_3SiOSi(CH_3)_3$, also referred to as HMDS), hexaethyl disiloxane ($(H_5C_2)_3SiOSi(C_2H_5)_3$) 1,1,3,3-tetramethyldisiloxane ($(H_3C)_2HSiOSi(CH_3)_2H$) and pentamethyl disiloxane (($H_3C)_3SiOSi(CH_3)_2H$) and the like, for example. One type of the disiloxane compound may be used alone, or two or more types of the disiloxane compound may be mixed and used. Among them, it is preferable to use hexamethyl disiloxane as the disiloxane compound since hexamethyl disiloxane is relatively inexpensive and easily available, and since hexamethyl disiloxane is easy to handle due to its safety, stability and boiling point comparable to those of water.

The reaction of the fluorine ion and the disiloxane compound is represented by the following formula (I).

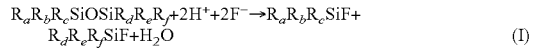

$$R_aR_bR_cSiOSiR_dR_eR_f + 2H^+ + 2F^- \rightarrow R_aR_bR_cSiF + R_dR_eR_fSiF + H_2O \quad (I)$$

In a case where the disiloxane compound is hexamethyl disiloxane (HMDS), in other words, in a case where $R_a$ to $R_f$ are all methyl group, the monofluorosilane compound formed by the reaction of the formula (I) is trimethylfluorosilane (hereinafter, also referred to as TMFS). Since the disiloxane compound is insoluble in water, the disiloxane compound is immiscible with the fluorine-containing aqueous solution, and thus, the disiloxane compound and the fluorine-containing aqueous solution are phase-separated into an organic phase comprising the disiloxane compound (a light liquid) and a water phase comprising the fluorine-containing aqueous solution (a heavy liquid). Therefore, the reaction of the fluorine ion in the fluorine-containing aqueous solution and the disiloxane compound can proceed only at an interface between the organic phase and the aqueous phase. Furthermore, since the disiloxane compound is a stable compound, the reaction rate of the formula (I) is relatively slow, and it takes a long time for the reaction.

The present inventors have found that the reaction of the fluorine ion with the disiloxane compound is facilitated by mixing the fluorine-containing aqueous solution and the disiloxane compound in a vertical direction, allowing the reaction to proceed efficiently in a short time. This is considered to result from the mixing in the vertical direction causing a movement of the fluorine ion in the fluorine-containing aqueous solution and the disiloxane compound to a direction perpendicular to the interface between the aqueous phase and the organic phase so that an opportunity of a contact between the fluorine ion in the fluorine-containing aqueous solution and the disiloxane compound is increased drastically. In the present specification, "mixing in a vertical direction" means a mixing which causes a movement of the substance to be mixed in a vertical direction to such an extent that uniformly mixed state is achieved without phase separation between the aqueous phase and the organic phase. The direction of the movement of the substance to be mixed may comprise a component other than a component in the vertical direction. As a method for mixing in the vertical direction, various methods can be adopted such as applying an external force and utilizing gravity. Specifically, the method for mixing may include, for example, a mixing method with a nozzle, a mixing method by irradiation of ultrasonic wave and countercurrent contact method as described below. However, the method for mixing is not limited to these methods.

(Mixing Method with Nozzle)

Figure 2:
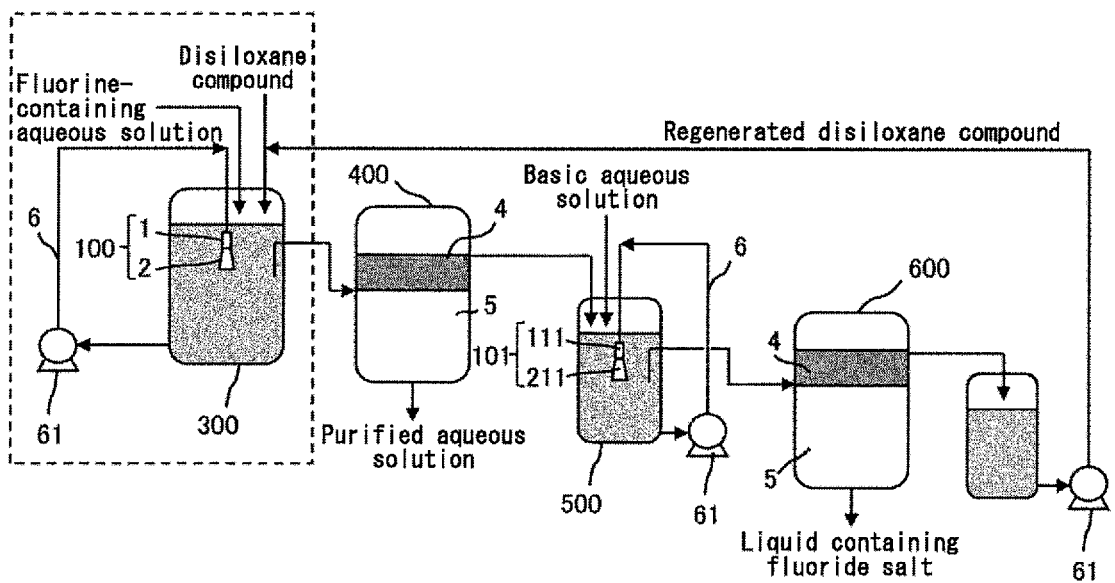
FIG. 2 is a schematic view of an apparatus according to an embodiment of the present invention.

In one embodiment of the present invention, the reaction step can be carried out in a first reaction vessel 300 shown in FIG. 2. The mixing in the vertical direction in the reaction step is carried out by ejecting a liquid taken out from the first reaction vessel 300, from a first ejection member 100 comprising a first nozzle 1 in the vertical direction in a liquid in the first reaction vessel 300. Taking out of the liquid from the first reaction vessel 300 can be carried out via a conduit 6. In some cases, a pump 61 may be used. In the present specification, "ejecting in a vertical direction" means an ejecting which causes a movement of the substance to be mixed in a vertical direction to such an extent that uniformly mixed state is achieved without phase separation between the aqueous phase and the organic phase. The direction of ejecting the liquid may comprise a component other than a component in the vertical direction. The direction of ejecting the liquid is determined by an attaching angle of the ejection member. The attaching angle is set to preferably from 0° to 60° and more preferably from 0° to 30° relative to the vertical direction (vertically upward direction or vertically downward direction). When the attaching angle of the ejection member is within the above-described range, the ejection in the vertical direction can be effectively provided, and the mixing in the vertical direction can be effectively achieved. The attaching angle is furthermore preferably 0° relative to the vertical direction (i.e., vertically upward direction or vertically downward direction). When the attaching angle of the ejection member is 0° relative to the vertical direction, the mixing in the vertical direction can be achieved furthermore effectively.

In the present specification, "nozzle" means a member attached to a tip of the conduit or the like, and narrowing an outlet of a fluid to form a jet (jet flow). The nozzle has an ejection opening (orifice) at the tip. The nozzle may also be referred to by a name such as a jet nozzle, an eductor and an ejector. The configuration of the nozzle which can be used in the present embodiment is not particularly limited as long as the nozzle has an inner diameter of the ejection opening (orifice) and a pressure resistance which are suitable for carrying out the mixing in the vertical direction. The inner diameter of the ejection opening and the ejection pressure will be described later.

Figure 3A:
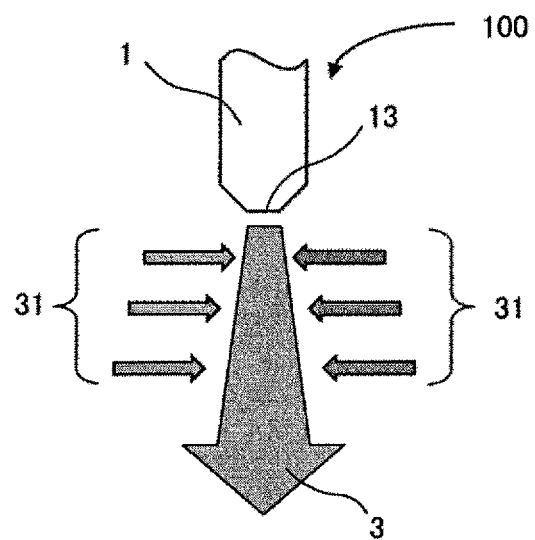
FIGS. 3A and 3B are schematic views of an ejection member in an embodiment of the present invention.

FIG. 3A schematically shows an ejection of a liquid from the ejection member 100. The liquid taken out from the first reaction vessel 300 is ejected from the tip 13 of the first nozzle 1 of the first ejection member 100 in the vertical direction into the liquid in the first reaction vessel 300. An ejection flow 3 ejected from the tip 13 of the nozzle 1 in the vertical direction forms a jet-like water flow (jet water flow). Such jet-like ejection flow 3 can increase its flow rate jetted in the vertical direction by engulfing (sucking) a liquid present on the side. The movement in the vertical direction of the liquid in the reaction vessel 300 can be achieved by this ejection flow 3 having a flow rate increased by the suction flow 31 from the side. As a result, the liquid in the reaction vessel 300 can be mixed in the vertical direction.

The mixing in the vertical direction in the reaction step is preferably carried out by ejecting a liquid taken out from a lower part of the first reaction vessel 300, from the first ejection member 100 comprising the first nozzle 1 in a vertically downward direction in an upper part of the liquid in the first reaction vessel 300. The mixing in the vertical direction can be further facilitated by taking out the liquid from the lower part of the first reaction vessel 300 and ejecting the taken-out liquid in the vertically downward direction in the upper part of the liquid in the first reaction vessel 300 in this manner. In addition, the disiloxane compound tends to be present in relatively larger amount in the upper part of the first reaction vessel 300 since the disiloxane compound has a specific gravity lower than that of water. Therefore, the ejection flow 3 can suck the disiloxane compound, which can be present in larger amount around the ejection flow 3, as the suction flow 31 from the side by ejecting the liquid from the first nozzle 1 of the first ejection member 100 in the vertically downward direction in the upper part of the liquid in the first reaction vessel 300. As a result, the jet in the vertically downward direction with the suction flow 31 added thereto which can contain large amount of the disiloxane compound is achieved, and the movement of the disiloxane compound in the vertical direction is facilitated. The first ejection member 100 is preferably placed in the upper part of the liquid in the first reaction vessel in order to achieve such effective mixing.

Alternatively, the mixing in the vertical direction in the reaction step can also be carried out by ejecting a liquid taken out from an upper part of the first reaction vessel 300, from the first ejection member 100 comprising the first nozzle 1 in a vertically upward direction in a lower part of the liquid in the first reaction vessel 300. The mixing in the vertical direction can be facilitated by taking out the liquid from the upper part of the first reaction vessel 300 and ejecting the taken-out liquid in the vertically upward direction in the lower part of the liquid in the first reaction vessel 300 in this manner. In addition, water-soluble fluorine ion tends to be present in relatively larger amount in the lower part of the liquid in the first reaction vessel 300 since the disiloxane compound has a specific gravity lower than that of water. Therefore, when the liquid is ejected from the first nozzle 1 of the first ejection member 100 in the vertically upward direction in the lower part of the liquid in the first reaction vessel 300, the ejection flow can suck a suction flow containing relatively larger amount of the water-soluble fluorine ion from the side. As a result, the jet in the vertically upward direction with the suction flow added thereto which has relatively high content of the fluorine ion is achieved, and thus, the movement of the fluorine ion in the vertical direction is facilitated. The first ejection member 100 may be placed in the lower part of the liquid in the first reaction vessel in order to achieve such effective mixing. When the liquid is ejected in the vertically upward direction from the first nozzle 1 of the first ejection member 100 in the lower part of the liquid in the first reaction vessel 300, the ejection flow 3 and the suction from 31 from the side can be represented by a diagram obtained by rotating FIG. 3 by 180°.

More preferably, assuming that a total volume of an organic component contained in the liquid in the first reaction vessel 300 is located on a total volume of an aqueous component contained in the liquid in the first reaction vessel 300, the first ejection member 100 is arranged such that a tip 13 of the first nozzle 1 is located in the organic component.

Figure 3B:
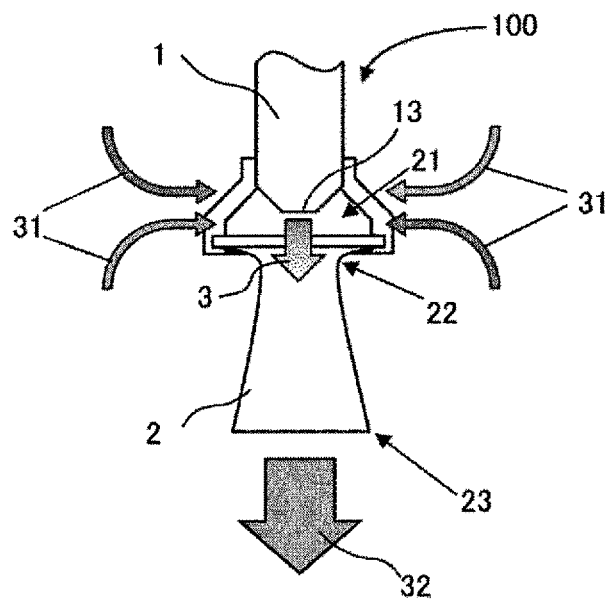
Figure 4:
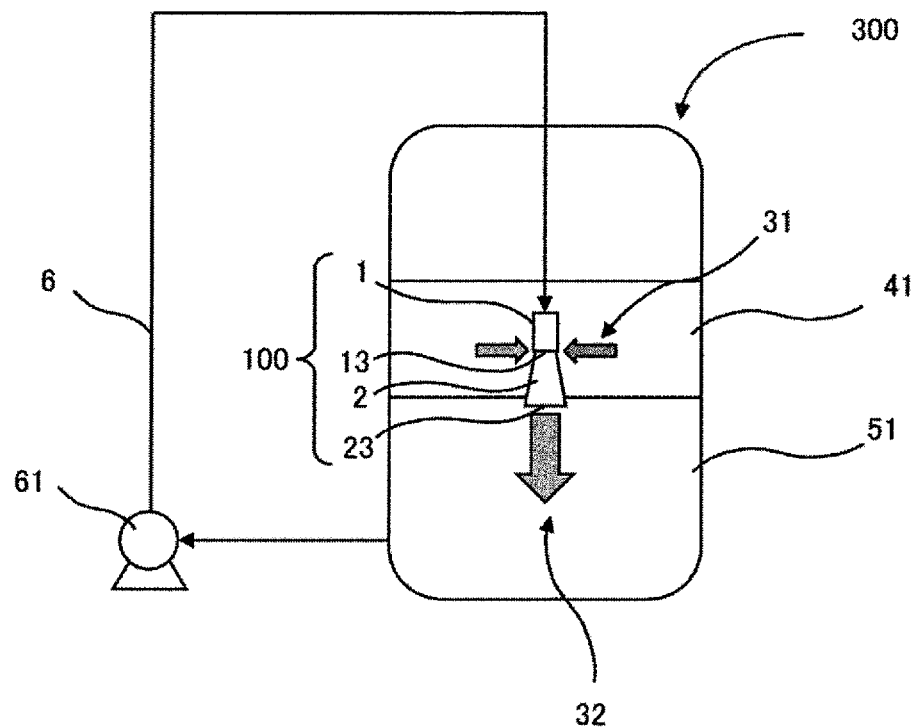
FIG. 4 is a schematic view showing an example of an arrangement of the ejection member in an embodiment of the present invention.

Assuming that the mixing in the vertical direction is stopped at one point in the reaction step, the liquid in the first reaction vessel 300 is considered to be phase-separated into an organic phase on the upper side and an aqueous phase on the lower side. Such virtual phase separation can be represented by a model where the total volume of the organic component (41) contained in the liquid in the first reaction vessel 300 is located on the total volume of the aqueous component (51) contained in the liquid in the first reaction vessel 300, as shown in FIG. 4. The first ejection member is preferably arranged such that the tip 13 of the first nozzle 1 is located in the organic component 41 in a case of assuming such a model. The disiloxane compound tends to be present in relatively larger amount in an area occupied by this virtual organic component 41 since the disiloxane compound has a specific gravity lower than that of water. Therefore, when the first ejection member 100 is arranged such that the tip 13 of the first nozzle 1 is located in this virtual organic component 41, the ejection flow ejected from the tip 13 of the nozzle 1 in the vertically downward direction (indicated by reference sign 3 in FIG. 3) can suck the disiloxane compound, which can be present in larger amount around the ejection flow 3, as the suction flow 31 from the side. As a result, the jet in the vertical direction with the suction flow 31 added thereto which can contain large amount of the disiloxane compound is achieved, and thus, the movement of the disiloxane compound in the vertical direction is facilitated. In this manner, an effective mixing in the vertical direction can be achieved.

Also, assuming the above-described model, the mixing in the vertical direction in the reaction step is preferably carried out by ejecting a liquid taken out from a lower part of the aqueous component 51, from the first ejection member 100 in a vertically downward direction, the first ejection member 100 being arranged such that the tip 13 of the first nozzle 1 is located in the organic component 41. By setting a position from which the liquid is taken out to the lower part of the virtual aqueous component 51, the taken-out liquid contains relatively larger amount of the aqueous component which has a specific gravity higher than that of the organic component. The water-soluble fluorine ion is present mainly in the aqueous component. Accordingly, the ejection flow containing relatively larger amount of the fluorine ion is ejected in the vertically downward direction from the tip 13 of the first nozzle 1 located in the virtual organic component 41 by this configuration, and thus, the movement of the fluorine ion in the vertical direction is facilitated. In this manner, the mixing in the vertical direction can be carried out furthermore effectively.

Figure 5:
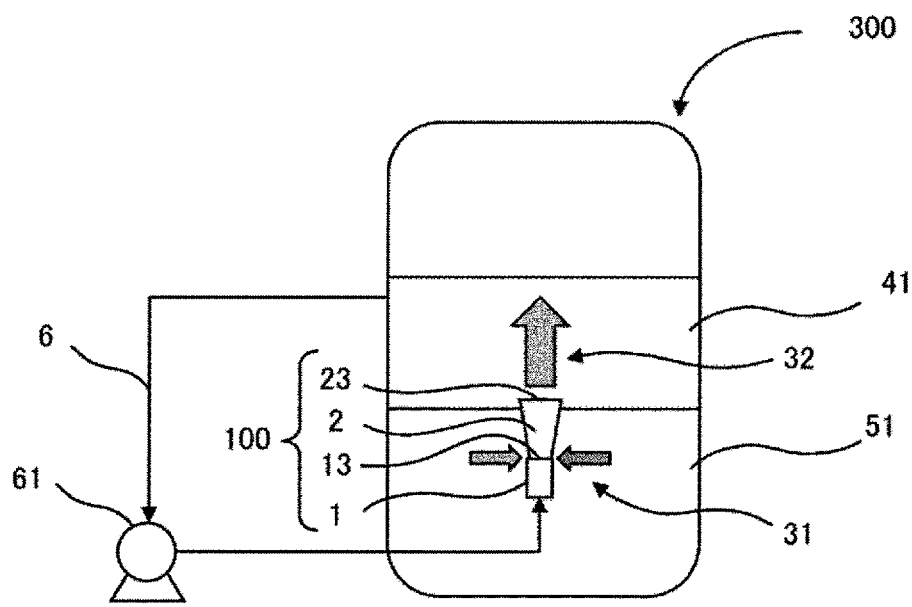
FIG. 5 is a schematic view showing another example of the arrangement of the ejection member in an embodiment of the present invention.

Alternatively, when the mixing in the vertical direction in the reaction step is carried out by ejecting the liquid taken out from the upper part of the first reaction vessel 300, from the first ejection member 100 comprising the first nozzle 1 in the vertically upward direction in the lower part of the liquid in the first reaction vessel 300, the first ejection member 100 may be arranged such that the tip 13 of the first nozzle 1 is located in the aqueous component 51 as shown in FIG. 5 in the virtual model described above. The water-soluble fluorine ion tends to be present in relatively larger amount in an area occupied by the virtual aqueous component 51. Therefore, when the first ejection member 100 is arranged such that the tip 13 of the first nozzle 1 is located in this virtual aqueous component 51, the ejection flow ejected from the tip 13 of the nozzle 1 in the vertically upward direction can suck a suction flow from the side which has relatively high content of the fluorine ion. As a result, the jet in the vertically upward direction with the suction flow added thereto which has relatively high content of the fluorine ion is achieved, and thus, the movement of the fluorine ion in the vertical direction is facilitated. In this manner, an effective mixing in the vertical direction can be achieved. In addition, when the first ejection member 100 is arranged such that the tip 13 of the first nozzle 1 is located in the aqueous component 51, it is preferable to eject the liquid taken out from the upper part of the organic component 41, from the first election member 100 in the vertically upward direction. By setting a position from which the liquid is taken out to the upper part of the virtual organic component 41, the taken-out liquid contains relatively larger amount of the organic component. As a result, the ejection flow containing relatively larger amount of the organic component is ejected in the vertically upward direction from the tip 13 of the first nozzle 1 located in the virtual aqueous component 51, and thus, the movement of the disiloxane compound in the organic component in the vertical direction can be carried out furthermore effectively.

As an example, when the reaction step is carried out in a batch-wise way, the fluorine-containing aqueous solution and the disiloxane compound put into the first reaction vessel 300 are phase-separated into an organic phase on the upper side containing the disiloxane compound and a aqueous phase on the lower side before the start of mixing. The virtual organic component 41 described above corresponds to the organic phase before the start of mixing, and the virtual aqueous component 51 corresponds to the aqueous phase before the start of mixing. In this case, the movement of the organic phase containing the disiloxane compound in the vertical direction can be facilitated by arranging the first ejection member 100 before the start of mixing such that the tip 13 of the first nozzle 1 is located in the organic phase, and the mixing in the vertical direction can be carried out more effectively. Furthermore, the movement of the fluorine ion in the aqueous phase in the vertical direction can be facilitated by setting a position from which the liquid ejected from the first ejection member 100 is taken out to the lower part of the aqueous phase before the start of mixing, and the mixing in the vertical direction can be carried out furthermore effectively.

Alternatively, when the mixing in the vertical direction in the reaction step is carried out by ejecting the liquid taken out from the upper part of the first reaction vessel 300, from the first ejection member 100 comprising the first nozzle 1 in the vertically upward direction in the lower part of the liquid in the first reaction vessel 300, in the batch-wise reaction step, the first ejection member 100 may be arranged before the start of mixing such that the tip 13 of the first nozzle 1 is located in the aqueous phase, and the position from which the liquid ejected from the first ejection member 100 is taken out may be set to the upper part of the organic phase before the start of mixing. The mixing of the liquid in the first reaction vessel 300 in the vertical direction can also be carried out effectively by such configuration.

The first ejection member 100 preferably further comprises a first diffuser 2 attached to the tip 13 of the first nozzle 1. FIG. 3B schematically shows an example of the first ejection member 100 comprises the first nozzle 1 and the first diffuser 2. The first diffuser 2 has one or more openings 21 on the side of the tip 13 of the first nozzle 1. The inner diameter at the tip 23 of the diffuser 2 is usually larger than the inner diameter at the end 22 on the opening side of the diffuser 2.

Due to the diffuser 2 having the opening(s) 21, the liquid present in the periphery of the ejection member 100 can be sucked as the suction flow 31 efficiently over a wide area from the opening(s) 21. As a result, the flow rate of the jet 32 from the tip 23 of the diffuser 2 is increased, and the mixing of the liquid in the first reaction vessel 300 in the vertical direction can be carried out furthermore effectively. The flow rate of the suction flow 31 from the side of the ejection flow 3 is preferably from 3 to 5 times larger than that of the ejection flow 3. This allows the flow rate of the jet 32 from the tip 23 of the diffuser 2 to be sufficiently large value.

Assuming that the total volume of the organic component (41) contained in the liquid in the first reaction vessel 300 is located on the total volume of the aqueous component (51) contained in the liquid in the first reaction vessel 300, the first ejection member 100 comprising the first nozzle 1 and the first diffuser 2 is preferably arranged such that the tip 13 of the first nozzle 1 is located in the organic component 41. FIG. 4 shows an example of the arrangement of the first ejection member 100. Assuming that the mixing in the vertical direction is stopped at one point in the reaction steps as described above, the liquid in the first reaction vessel 300 is phase-separated into the organic phase on the upper side and the aqueous phase on the lower side. Such virtual phase separation can be represented by a model where the total volume of the organic component 41 contained in the liquid in the first reaction vessel is located on the total volume of the aqueous component 51 contained in the liquid in the first reaction vessel. The disiloxane compound tends to be present in relatively larger amount in an area occupied by this virtual organic component 41 since the disiloxane compound has a specific gravity lower than that of water. Therefore, the suction flow 31 from the side which can contain large amount of the disiloxane compound can be sucked from the opening(s) 21 of the first diffuser 2 due to the tip 13 of the first nozzle 1 located in this virtual organic component 41. The movement of the disiloxane compound in the vertical direction is furthermore facilitated by the jet 32 with the suction flow 31 added thereto which can contain large amount of the disiloxane compound being ejected in the vertically downward direction toward the aqueous component 51 from the tip 23 of the first diffuser 2, and thus, the mixing in the vertical direction can be carried out furthermore effectively.

Alternatively, when assuming the virtual model described above, the first ejection member 100 comprising the first nozzle 1 and the first diffuser 2 is preferably arranged such that the tip 13 of the first nozzle 1 is located in the aqueous component 51. FIG. 5 shows an example of the arrangement of the first ejection member 100. The water-soluble fluorine ion tends to be present in relatively larger amount in an area occupied by the virtual aqueous component 51. Thus, the suction flow 31 from the side which can contain relatively large amount of the fluorine ion can be sucked from the opening(s) 21 of the first diffuser 2 due to the tip 13 of the first nozzle 1 located in this virtual aqueous component 51. The movement of the fluorine ion in the vertical direction is furthermore facilitated by the jet 32 with the suction flow 31 added thereto which has relatively high content of the fluorine ion being ejected from the tip 23 of the first diffuser 2 in the vertically upward direction toward the organic component 41, and thus, the mixing in the vertical direction can be carried out furthermore effectively.

The mixing in the vertical direction in the reaction step is facilitated as a linear velocity of the ejection flow at the tip 13 of the first nozzle 1 is larger. The linear velocity of the ejection flow can be controlled by the inner diameter of the tip 13 of the first nozzle 1 and the flow rate (or the ejection pressure) of the ejection flow. The linear velocity of the ejection flow at the tip 13 of the first nozzle 1 is preferably from 500 to 2000 m/min. When the linear velocity of the ejection flow is 500 m/min or more, the mixing in the vertical direction can be carried out more effectively. When the linear velocity of the ejection flow is 2000 m/min or less, the mixing can be carried out with an ejection pressure at which it is not necessary to apply a special pressure-resistant specification to the nozzle, and thus, the equipment cost can be reduced. The first nozzle 1 may be used alone, or a plurality of the first nozzles 1 may be provided in the first reaction vessel 300. It is possible to achieve high linear velocity as a whole while reducing the linear velocity per nozzle by use of a plurality of the first nozzles 1.

The inner diameter at the tip (ejection opening) of the nozzle and the ejection pressure can be set appropriately so as to achieve the linear velocity described above. The inner diameter at the tip of the nozzle is preferably from 1.5 mm to 20 mm. When the inner diameter is 1.5 mm or more, the mixing in the vertical direction can be effectively achieved. When the inner diameter is 20 mm or less, the mixing can be carried out with an ejection pressure at which it is not necessary to apply a special pressure-resistant specification to the nozzle, and thus, the equipment cost can be reduced. The ejection pressure is preferably from 0.05 to 0.8 MPa. The ejection pressure of 0.05 MPa or more can effectively achieve the mixing in the vertical direction. When the ejection pressure is 0.8 MPa or less, it is not necessary to apply a special pressure-resistant specification to the nozzle, and thus, the equipment cost can be reduced.

Although the reaction step is carried out continuously in the embodiment shown in FIG. 2, the reaction step according to the present invention can be carried out in any of a batch-wise way and a continuous way.

(Mixing Method by Ultrasonic Irradiation)

Figure 6:
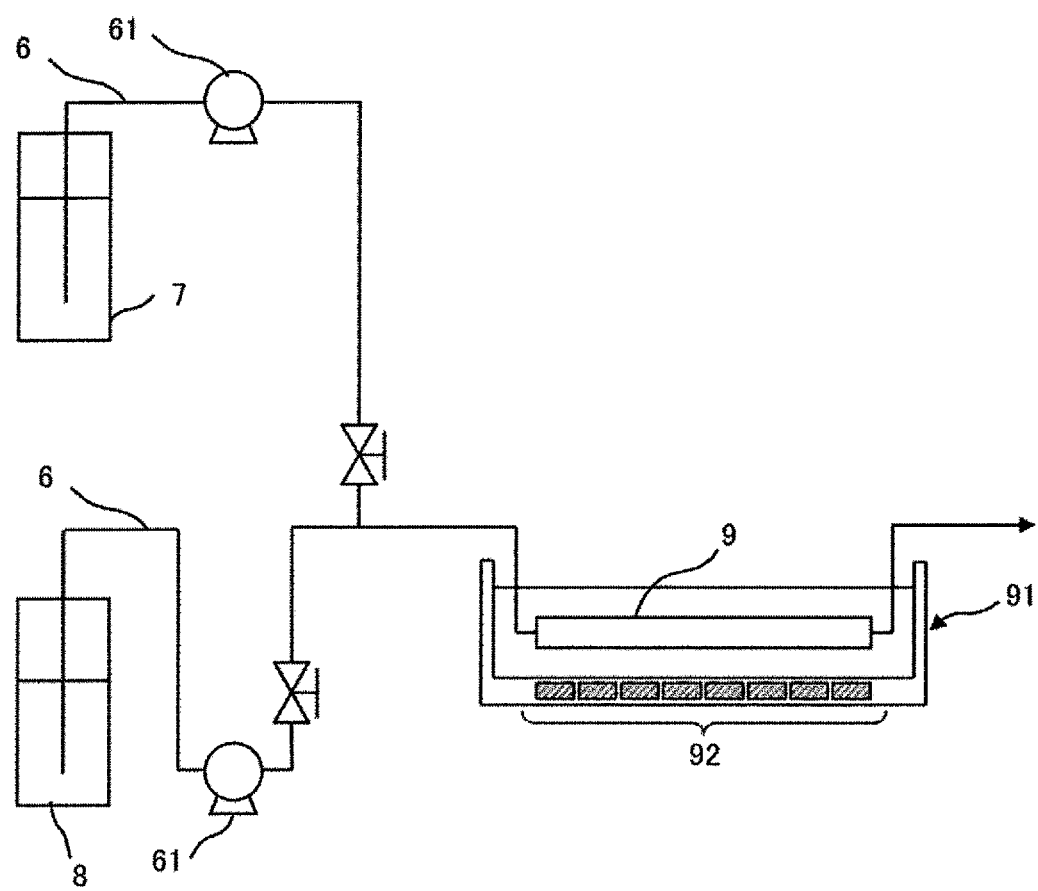
FIG. 6 is a schematic view of a tubular reactor in an embodiment of the present invention.

In another embodiment of the present invention, the mixing in the vertical direction in the reaction step is carried out by irradiating the fluorine-containing aqueous solution and the disiloxane compound with ultrasonic wave. An example of mixing by ultrasonic irradiation is shown in FIG. 6. The mixing by the ultrasonic waves can be carried out by carrying out the reaction step with a first tubular reactor 9 shown in FIG. 6 instead of the reaction step with the first reaction vessel 300 in FIG. 2 (a portion surrounded by a broken line in the drawing).

In the embodiment shown in FIG. 6, the first tubular reactor 9 is provided in an ultrasonic generator 91. The ultrasonic generator 91 includes a vibrator 92 arranged in the lower portion of the first tubular reactor along the flow direction in the first tubular reactor. A medium such as pure water is filled in the ultrasonic generator 91. The disiloxane compound (7) and the fluorine-containing aqueous solution (8) are continuously fed to the tubular reactor 9 provided in the ultrasonic generator 91 through a conduit 6 a pump 61. The fluorine-containing aqueous solution and the disiloxane compound flowing inside the first tubular reactor 9 are irradiated with the ultrasonic wave generated by the vibrator 92 through the medium. In this embodiment, the ultrasonic wave is emitted perpendicularly to the direction of flow inside the first tubular reactor. A vibration generated by the ultrasonic wave and a shock wave generated by rapture of a bubble formed by the ultrasonic wave (shock wave by cavitation) make at least a part of the fluorine-containing aqueous solution and the disiloxane compound in the first tubular reactor 9 into a form of fine liquid droplets. The mixing in the vertical direction is achieved by such droplets moving inside the first tubular reactor 9 due to an action such as the vibration by the ultrasonic wave and convection.

The vibrator 92 is preferably arranged so as not to have contact with the liquid inside the first tubular reactor 9 as shown in FIG. 6. When the vibrator 92 is arranged so as to have contact with the liquid inside the first tubular reactor 9 (for example, when the vibrator 92 is arranged inside the first tubular reactor 9), there is a risk of wearing of the vibrator 92 depending on the composition of the liquid. In addition, when the vibrator 92 is arranged so as to have contact with the liquid inside the first tubular reactor 9, ultrasonic wave oscillating from the vibrator 92 is reflected on a tube wall of the first tubular reactor 9, causing an occurrence of sympathetic vibration. This sympathetic vibration also facilitates the wearing of the vibrator 92. The wearing of the vibrator 92 is suppressed by arranging the vibrator 92 so as not to have contact with the liquid in the first tubular reactor 9, and thus, the replacement cost of the vibrator 92 can be reduced.

Frequency of the ultrasonic wave emitted by the vibrator 92 is preferably set to from 20 kHz to 1 MHz. In a case where the frequency is 20 kHz or more, the mixing by the irradiation of the ultrasonic wave can be carried out more effectively. In a case where the frequency is 1 MHz or less, damping of the ultrasonic wave is small, and thus, a reaching distance of the ultrasonic wave can be sufficiently long.

The mixing method using such a tubular reactor 9 and an ultrasonic generator 91 also has an advantage that mixing and reaction of the fluorine-containing aqueous solution and the disiloxane compound can be carried out in a single pass.

The mixing by the irradiation of the ultrasonic wave is not intended to be limited to the embodiment shown in FIG. 6. Although the reaction step is carried out in continuously in the embodiment shown in FIG. 6, the mixing by the irradiation of the ultrasonic wave can also be carried out in batch-wise way.

(Mixing Method by Countercurrent Contact Method)

Figure 7:
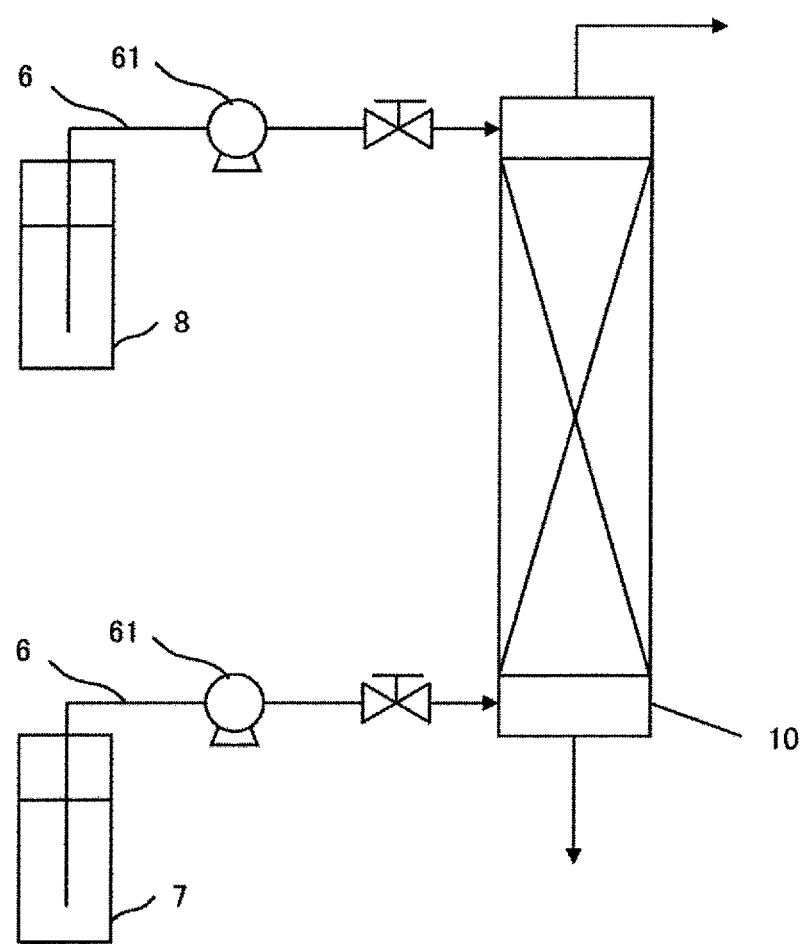
FIG. 7 is a schematic view of a countercurrent reaction column in an embodiment of the present invention.

In yet another embodiment of the present invention, the mixing in the vertical direction in the reaction step can also be carried out by a countercurrent contact method. The mixing by the countercurrent contact method can be carried out in a first countercurrent reaction column, an organic phase comprising the disiloxane compound and the monofluorosilane compound is obtained at the top of the first countercurrent reaction column, and a purified aqueous solution with reduced fluorine concentration compared to the fluorine-containing aqueous solution is obtained at the bottom of the first countercurrent reaction column. An example of the mixing by the countercurrent contact method is shown in FIG. 7. In the example shown in FIG. 7, the mixing by the countercurrent contact method is carried out in a first countercurrent reaction column 10 filled with a packing. The packing which can be used in the present embodiment is not particularly limited, and the packing such as Raschig rings and a demister can be used appropriately. The fluorine-containing aqueous solution 8 is fed to the upper part of the first countercurrent reaction column 10 via a conduit 6 and a pump 61. On the other hand, the disiloxane compound 7 is fed to the lower part of the first countercurrent reaction column 10 via a conduit 6 and a pump 61. A feed rate and a residence time of the fluorine-containing aqueous solution 8 and disiloxane compound 7 can be set appropriately depending on an apparatus to be used or the like. Since the disiloxane compound has a specific gravity lower than that of water, the fluorine-containing aqueous solution fed to the upper part of the reaction column 10 moves in a downward direction inside the reaction column 10 by the action of gravity, while the disiloxane compound fed to the lower part of the reaction column 10 moves in an upward direction inside the reaction column 10. An opportunity of a contact between the fluorine ion and the disiloxane compound is increased by such a movement of the disiloxane compound and the fluorine-containing aqueous solution in the vertical direction so that the reaction can proceed effectively. As a result of carrying out the countercurrent contact of the disiloxane compound with the fluorine-containing aqueous solution in this manner, the organic phase comprising the disiloxane compound and the monofluorosilane compound can be obtained at the top of the reaction column, while the purified aqueous solution with reduced fluorine concentration compared to the fluorine-containing aqueous solution can be obtained at the bottom of the reaction column.

When the mixing in the vertical direction in the reaction step is carried out by the countercurrent contact method, it is also possible to use a first countercurrent reaction column comprising therein an agitator vibrating vertically, instead of the first countercurrent reaction column 10 filled with the packing described above. In this embodiment, the fluorine-containing aqueous solution is fed to the upper part of the reaction column, while the disiloxane compound is fed to the lower part of the reaction column. The agitator may be, for example, a large number of perforated plates attached in the reaction column, and vertical vibration is applied to the liquid in the reaction column by the vertical vibration of the perforated plates so that the mixing of the liquid in the vertical direction can be achieved. As the first countercurrent reaction column comprising therein the agitator vibrating vertically, a reciprocating extraction column, a continuous liquid-liquid extraction apparatus and the like can be used, for example.

The reaction step in the present invention has an advantage of not requiring additional operation for adjusting pH of the liquid to be processed. However, the progress of the reaction can be facilitated in acidic condition since the reaction represented by the above formula (I) is activated by a proton. Therefore, the fluorine-containing aqueous solution is preferably an acidic aqueous solution.

The fluorine-containing aqueous solution which can be processed by the processing method according to the present invention is not particularly limited as described above, and the method according to the present invention can be applied to the processing of various aqueous solutions containing fluorine. The fluorine-containing aqueous solution may be a fluorine-containing hydrochloric acid, a fluorine-containing sulfuric acid and a mixture thereof, for example. The method according to the present invention has a surprising effect of allowing the fluorine ion to selectively react with the disiloxane compound to selectively remove the fluorine ion even in an aqueous solution in which a large amount of chloride ions are present such as fluorine-containing hydrochloric acid. Furthermore, in a case of processing an acidic fluorine-containing aqueous solution such as fluorine-containing hydrochloric acid, the method according to the present invention can process the aqueous solution without changing its acid concentration before and after the reaction step. For example, when fluorine-containing hydrochloric acid is processed by the method according to the present invention, an acid concentration (concentration of hydrogen chloride) in the hydrochloric acid is not substantially changed before and after the reaction step.

In a case where the fluorine-containing aqueous solution is an acidic aqueous solution, the reaction step in the present invention can be carried out even with any value of the acid concentration, and has an advantage of not requiring additional operation for adjusting the acid concentration. However, the fluorine-containing aqueous solution preferably has an acid concentration of 0.1% or more by weight since the reaction represented by the formula (I) can be further facilitated. The acid concentration of the fluorine-containing aqueous solution is more preferably from 10 to 40% by weight. In the reaction represented by the formula (I), $H^+$ is considered to have a catalytic effect. Therefore, the effect is expected to be increased as the existing amount of $H^+$ is larger, i.e., as the acid concentration is higher. In a case where the acid concentration is 10% or more by weight, the reaction represented by the formula (I) can be further facilitated. In a case where the acid concentration exceeds 40% by weight, the catalytic effect of $H^+$ is substantially constant without depending on the acid concentration. Therefore, in a case where the acid concentration is 40% or less by weight, the amount of acid required for adjusting the acid concentration can be reduced while achieving sufficient catalytic effect.

The reaction step in the present invention can be carried out at ambient temperature, and has an advantage of not requiring temperature control which requires cost. However, it is preferable to carry out the reaction step at a temperature of 50° C. or more since the reaction represented by the above formula (I) can be further facilitated. Also, the reaction of the formula (I) can proceed further by carrying out the reaction step under pressure.

In the method according to the present invention, the disiloxane compound is a reactant for reacting with the fluorine ion in the fluorine-containing aqueous solution to form the monofluorosilane compound, and also a solvent for extracting the formed monofluorosilane compound from the aqueous phase. Sufficient amount of the disiloxane compound used as the reactant would be at least 0.5 molar equivalent relative to the fluorine ion in the fluorine-containing aqueous solution as can be seen from the above formula (I). Considering the amount of the disiloxane compound required as the solvent, a molar ratio of the disiloxane compound used in the reaction step to the fluorine ion in the fluorine-containing aqueous solution is preferably from 0.5 to 20. In a case where the molar ratio is 0.5 or more, the disiloxane compound is present in stoichiometric amount or more relative to the fluorine ion present in the fluorine-containing aqueous solution, and the reaction of the formula (I) can proceed. In a case where the molar ratio is 20 or less, a processing amount of the fluorine-containing aqueous solution in the reaction step can be made into practically sufficient amount, and higher processing efficiency can be achieved.

[The First Separation Step]

The method according to the present invention optionally comprises a first separation step. The first separation step is a step for separating the first reaction liquid obtained in the reaction step into an organic phase and an aqueous phase. Since the monofluorosilane compound formed in the reaction step and unreacted disiloxane compound are insoluble in water, the organic phase contains the disiloxane compound and the monofluorosilane compound, and the aqueous phase is substantially free of the disiloxane compound and the monofluorosilane compound. In the first separation step, the aqueous phase can be obtained as a purified aqueous solution with reduced fluorine concentration compared to the fluorine-containing aqueous solution. In the case where the mixing in the reaction step is carried out by the countercurrent contact method, the first separation step is unnecessary.

In one embodiment, the first separation step is carried out in a first separation vessel 400 shown in FIG. 2. The first separation step can be carried out continuously as shown in FIG. 2; however, it can also be carried out in a batch-wise way. When the reaction step and the first separation step are carried out in a batch-wise way, the first reaction vessel 300 can be used as the first separation vessel 400. That is, the reaction step is carried out in the first reaction vessel 300, and then, the first separation step can be carried out by stopping mixing and by leaving the liquid to stand in the first reaction vessel 300 to phase-separate the liquid.

The first reaction liquid obtained in the reaction step is phase-separated quickly when the first reaction liquid is introduced into the first separation vessel 400. Therefore, the first separation step in the present invention does not require additional operation which can cause an increased cost. The organic phase 4 on the upper side contains the disiloxane compound and the monofluorosilane compound. The aqueous phase 5 on the lower side is substantially free of the disiloxane compound and the monofluorosilane compound. In the present specification, "substantially free" of a compound means that the content of the compound is 300 ppm or less.

After the phase separation, the aqueous phase 5 is obtained as the purified aqueous solution with reduced fluorine concentration compared to the fluorine-containing aqueous solution. According to the method of the present invention, the fluorine concentration in the purified aqueous solution can be reduce to 1000 ppm or less, preferably 500 ppm or less and more preferably 100 ppm or less. As described above, the reaction step in the method according to the present invention can selectively react the fluorine ion with the disiloxane compound to selectively remove the fluorine ion even in an aqueous solution in which a large amount of chloride ions are present. Therefore, the purified aqueous solution such as purified hydrochloric acid can be obtained in the first separation step without changing the acid concentration before and after the reaction step. For example, when the fluorine-containing hydrochloric acid is processed by the method according to the present invention, purified hydrochloric acid having substantially the same acid concentration (hydrogen chloride concentration) as the acid concentration of the fluorine-containing hydrochloric acid before the reaction step can be obtained in the first separation step.

[Regeneration Process]

The method according to the present invention optionally further comprises a regeneration step and a second separation step. The regeneration step is a step for reacting the monofluorosilane compound, which is formed by the reaction of the fluorine ion in the fluorine-containing aqueous solution with the disiloxane compound, with a base to regenerate the monofluorosilane compound into the disiloxane compound.

In the regeneration step, the organic phase obtained in the first separation step (or the reaction step in a case where the reaction step is carried out by the countercurrent contact method) is mixed with a basic aqueous solution, and thereby the monofluorosilane compound contained in the organic phase is reacted with the base contained in the basic aqueous solution to obtain a second reaction liquid containing the disiloxane compound and a fluoride salt. The reactions in the regeneration step are represented by the following formulas (II) and (III-1) to (III-3).

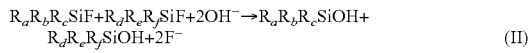

$$R_aR_bR_cSiF + R_dR_eR_fSiF + 2OH^- \rightarrow R_aR_bR_cSiOH + R_dR_eR_fSiOH + 2F^- \quad (II)$$

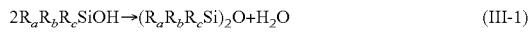

$$2R_aR_bR_cSiOH \rightarrow (R_aR_bR_cSi)_2O + H_2O \quad (III\text{-}1)$$

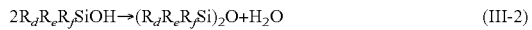

$$2R_dR_eR_fSiOH \rightarrow (R_dR_eR_fSi)_2O + H_2O \quad (III\text{-}2)$$

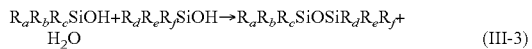

$$R_aR_bR_cSiOH + R_dR_eR_fSiOH \rightarrow R_aR_bR_cSiOSiR_dR_eR_f + H_2O \quad (III\text{-}3)$$

When HMDS is used as the disiloxane compound, the monofluorosilane compound formed by the reaction of the formula (I) in the reaction step is TMFS. In this case, TMFS is regenerated into HMDS via trimethylsilanol in the regeneration step.

The reactions of the formulas (II) and (III-1) to (III-3) can proceed easily compared to the reaction of the formula (I) in the reaction step since the monofluorosilane compound is relatively unstable in basic condition. Therefore, a mixing in the regeneration step may not be a mixing in the vertical direction, and any mixing technique such as mixing by a mixer such as a static mixer can be employed appropriately. However, it is preferable to carry out the mixing in the vertical direction in the regeneration step since the reactions of the formulas (II) and (III-1) to (III-3) can be furthermore facilitated by mixing the organic phase obtained in the first separation step with the basic aqueous solution in the vertical direction. The mixing in the vertical direction of the organic phase and the basic aqueous solution in the regeneration step is preferably carried out in a manner similar to the mixing in the vertical direction in the reaction step as described above.

For example, in one embodiment, the regeneration step can be carried out in a second reaction vessel 500 shown in FIG. 2. In the embodiment shown in FIG. 2, the second reaction vessel 500 comprises a conduit 6 and a pump 61. The mixing in the vertical direction in the regeneration step is preferably carried out by ejecting a liquid taken out from the second reaction vessel 500, from a second ejection member 101 comprising a second nozzle 111 in a vertical direction in a liquid in the second reaction vessel 500. This can facilitate the progress of the reactions represented by the formulas (II) and (III-1) to (III-3).

The mixing in the vertical direction in the regeneration step is preferably carried out by ejecting a liquid taken out from a lower part of the second reaction vessel 500, from the second ejection member 101 comprising the second nozzle 111 in a vertically downward direction in an upper part of the liquid in the second reaction vessel 500. The mixing in the vertical direction of the liquid in the second reaction vessel 500 can be further facilitated by mixing in this manner.

Alternatively, the mixing in the vertical direction in the regeneration step may be carried out by ejecting a liquid taken out from an upper part of the second reaction vessel 500, from the second ejection member 101 comprising the second nozzle 111 in a vertically upward direction in a lower part of a liquid in the second reaction vessel 500. The mixing of the liquid in the second reaction vessel 500 in the vertical direction can also be carried out effectively with such a configuration.

More preferably, assuming that a total volume of an organic component contained in the liquid in the second reaction vessel 500 is located on a total volume of an aqueous component contained in the liquid in the second reaction vessel 500, the second ejection member 101 is arranged such that a tip of the second nozzle 111 is located in the organic component. Assuming that the mixing in the vertical direction is stopped at one point in the regeneration step, the liquid in the second reaction vessel 500 is considered to be phase-separated into an organic phase on the upper side and an aqueous phase on the lower side. Such virtual phase separation can be represented by a model where the total volume of the organic component (corresponding to 41 in FIG. 4) contained in the liquid in the second reaction vessel 500 is located on the total volume of the aqueous component (corresponding to 51 in FIG. 4) contained in the liquid in the second reaction vessel 500, as is the case with the virtual model in the reaction step shown in FIG. 4. Assuming such a model, the ejection flow ejected from the tip of the second nozzle 111 in the vertically downward direction can suck the monofluorosilane compound in the organic component, which can be present in larger amount around it, as the suction flow from the side by arranging the second ejection member 101 as described above. As a result, the jet flow in the vertical direction with the suction flow 31 added thereto which can contain large amount of the monofluorosilane compound is achieved, and thus, the movement of the monofluorosilane compound in the vertical direction is facilitated. In this manner, it is possible to achieve an effective mixing in the vertical direction.

Also, assuming the above-described model, the mixing in the vertical direction in the regeneration step is preferably carried out by ejecting a liquid taken out from a lower part of the aqueous component, from the second ejection member 101 in a vertically downward direction. The movement of the aqueous component in the vertical direction is facilitated by mixing with such configuration, and thus, the mixing of the liquid in the second reaction vessel 500 in the vertical direction can be carried out more effectively.

Furthermore, the second ejection member 101 may further comprise a second diffuser 211 attached to the tip of the second nozzle 111. The second diffuser 211 has one or more openings on the side of the tip 13 of the second nozzle 111. The mixing of the liquid in the second reaction vessel 500 in the vertical direction can be carried out more effectively by use of the second diffuser 211.

As the second nozzle 111 and the second diffuser 211, the same ones as the first nozzle 1 and the first diffuser 2 described above can be used.

The mixing in the vertical direction in the regeneration step is facilitated as a linear velocity of the ejection flow at the tip of the second nozzle 111 is larger, as is the case with the mixing in the vertical direction in the reaction step. The linear velocity of the ejection flow at the tip of the second nozzle 111 is preferably from 500 to 2000 m/min. When the linear velocity of the ejection flow is 500 m/min or more, the mixing in the vertical direction can be carried out more effectively. When the linear velocity of the ejection flow is 2000 m/min or less, the mixing can be carried out with an ejection pressure at which it is not necessary to apply a special pressure-resistant specification to the nozzle, and thus, the equipment cost can be reduced.

In another embodiment, the mixing in the vertical direction in the regeneration step may be carried out by irradiating the organic phase obtained in the first separation step (or the reaction step in a case where the reaction step is carried out by the countercurrent contact method) and the basic aqueous solution with ultrasonic wave. The mixing by the irradiation of ultrasonic wave in the regeneration step can be carried out in a manner similar to the mixing by the irradiation of ultrasonic wave in the reaction step as described above. For example, the regeneration process may be carried out in a second tubular reactor having a configuration similar to that of the first tubular reactor 9 shown in FIG. 6. In the second tubular reactor, ultrasonic wave is emitted by a vibrator arranged in the lower portion of the second tubular reactor along the flow direction in the second tubular reactor.

In yet another embodiment of the present invention, the mixing in the vertical direction in the regeneration step can also be carried out by the countercurrent contact method. The mixing by the countercurrent contact method can be carried out in a second countercurrent reaction column in which the organic phase obtained in the first countercurrent reaction column or the first separation vessel is fed to a lower part of the second countercurrent reaction column, the basic aqueous solution is fed to the upper part of the second countercurrent reaction column, an organic phase containing the disiloxane compound and substantially free of a fluoride salt is obtained at the top of the second countercurrent reaction column, and an aqueous phase containing the fluoride salt and substantially free of the disiloxane compound is obtained at the bottom of the second countercurrent reaction column. The mixing by the countercurrent contact method in the regeneration step may be carried out in a second countercurrent reaction column filled with a packing and having a structure similar to that of the first countercurrent reaction column which can be used for the countercurrent contacting method in the reaction step as described above. In the second countercurrent reaction column, the organic phase obtained in the reaction step or the first separation step is fed to the lower part of the second countercurrent reaction column via a conduit and a pump. On the other hand, the basic aqueous solution is fed to the upper part of the second countercurrent reaction column via a conduit and a pump. Since the organic phase has a specific gravity lower than that of water, the basic aqueous solution fed to the upper part of the reaction column moves in a downward direction inside the reaction column, while the organic phase fed to the lower part of the reaction column moves in an upward direction inside the reaction column. An opportunity of a contact between the monofluorosilane compound in the organic phase and the basic aqueous solution is increased by such a movement of both of the organic phase and the basic aqueous solution in the vertical direction so that the regeneration reaction can proceed effectively. As a result of carrying out the countercurrent contact in this manner, the organic phase containing the disiloxane compound and substantially free of a fluoride salt can be obtained at the top of the second countercurrent reaction column, while the aqueous phase containing the fluoride salt and substantially free of the disiloxane compound can be obtained at the bottom of the second countercurrent reaction column. The organic layer thus obtained can be recycled in the reaction step.

In a case where the mixing in the vertical direction in the regeneration step is carried out by the countercurrent contact method, it is also possible to use a second countercurrent reaction column comprising therein an agitator vibrating vertically, instead of the second countercurrent reaction column filled with the packing described above. As the second countercurrent reaction column comprising therein an agitator vibrating vertically, a column similar to the first countercurrent reaction column comprising therein an agitator vibrating vertically which can be used in the reaction step can be used. In this embodiment, the fluorine-containing aqueous solution is fed to the upper part of the reaction column, and a disiloxane compound is fed to the lower part of the reaction column. Vertical vibration is applied to the liquid in the reaction column by the vertical vibration of the agitator so that the mixing of the liquid in the vertical direction can be achieved.

As can be seen from the above formula (II), sufficient amount of the base contained in the basic aqueous solution used in the regeneration step would be at least 1 molar equivalent relative to the amount of the monofluorosilane compound contained in the organic phase obtained in the first separation step. A molar ratio of the base contained in the basic aqueous solution used in the regeneration step to the monofluorosilane compound contained in the organic phase obtained in the first separation step is preferably 1.3 or more and more preferably 1.5 or more. In a case where the molar ratio is 1.3 or more, the progress of the reactions of the formulas (II) and (III-1) to (III-3) can be facilitated. In a case where the molar ratio is 1.5 or more, the reaction rate of the monofluorosilane compound and the base can be close to 100 percent.

The basic aqueous solution has pH value of preferably 8 or more and more preferably from 13 to 14. In a case where the basic aqueous solution has pH value within the above range, the progress of the reactions of the formulas (II) and (III-1) to (III-3) can be facilitated. The basic aqueous solution may include, for example, lithium hydroxide aqueous solution, potassium hydroxide aqueous solution, sodium hydroxide aqueous solution, calcium hydroxide aqueous solution, magnesium hydroxide aqueous solution and a mixture thereof. In the regeneration reaction, the monofluorosilane compound is reacted with OH$^-$ ion in the basic aqueous solution to regenerate the disiloxane compound as shown in the formulas (II) and (III-1) to (III-3). In this regeneration reaction, dissociated fluorine ion forms a metal salt (such as LiF, KF, NaF, $CaF_2$ and $MgF_2$) with an alkali metal ion and/or an alkali earth metal ion contained in the basic aqueous solution. When the metal salt has high solubility, precipitation of insoluble metal salt can be prevented in the regeneration step and the subsequent second separation step, causing easy handling. When sodium hydroxide aqueous solution is used as the basic aqueous solution, precipitation of insoluble metal salt in the regeneration step and the second separation step can be prevented since the metal salt (NaF) formed in the regeneration step has relatively high solubility among the above-described metal salts. In addition, running cost can be reduced by use of sodium hydroxide aqueous solution. Therefore, it is preferable to use sodium hydroxide aqueous solution as the basic aqueous solution.

While the regeneration step is carried out continuously in the embodiment shown in FIG. 2, the regeneration step in the present invention can be carried out by in a batch-wise way. In a case where the mixing by irradiation of ultrasonic wave is carried out instead of the mixing by the second ejection member 101 shown in FIG. 2, the regeneration step can be carried out continuously by use of the configuration shown in FIG. 6 as described above; however, the mixing by irradiation of ultrasonic wave can also be carried out in a batch-wise way.

[Second Separation Step]

The second separation step is a step for phase-separating the second reaction liquid obtained in the regeneration step into an organic phase comprising the disiloxane compound and substantially free of fluoride salt and an aqueous phase comprising the fluoride salt and substantially free of disiloxane compound. In a case where the mixing in the regeneration step is carried out by the countercurrent contact method, the second separation step is unnecessary.

In one embodiment, the second separation step is carried out in a second separation vessel 600 shown in FIG. 2. The second separation step can be carried out continuously as shown in FIG. 2; however, it may also be carried out in a batch-wise way. When the regeneration step and the second separation step are carried out in a batch-wise way, the second reaction vessel 500 can be used as the second separation vessel 600. That is, the regeneration step is carried out in the second reaction vessel 500, and then, the second separation step can be carried out by stopping mixing and by leaving the liquid to stand in the second reaction vessel 500 to phase-separate the liquid.

The second reaction liquid obtained in the regeneration step is phase-separated quickly when the second reaction liquid is introduced into the second separation vessel 600. Therefore, the second separation step in the present invention does not require additional operation which can cause an increased cost. The organic phase 4 on the upper side contains the disiloxane compound and is substantially free of the fluoride salt. The aqueous phase 5 on the lower side contains the fluoride salt and is substantially free of the disiloxane compound. In a case where NaOH aqueous solution is used as the basic aqueous solution in the regeneration step, the fluoride salt is NaF.

After the phase separation, the aqueous phase 5 is obtained as a liquid containing the fluoride salt. The organic phase 4 obtained in the second separation step can be recycled in the reaction step as the disiloxane compound. For example, as shown in FIG. 2, the organic phase 4 obtained in the second separation vessel 600 can be recycled in the first reactor 300 as the disiloxane compound. Since the disiloxane compound can be regenerated and used repeatedly in the method according to the present invention in this manner, processing cost can be reduced.

Since any of the reaction step, the first separation step, the regeneration step and the second separation step does not involve substantial temperature rise and pressure rise, these steps can be carried out at ambient temperature and ambient pressure without controlling the temperature and the pressure.

EXAMPLES

Example 1. Dependence of Time Required for the Reaction Step on Mixing Method

In Tests 1 to 5 described below, the time required for the reaction step of the present application was examined by use of various mixing methods. Any of the Tests 1 to 5 was carried out at room temperature.
(Test 1)
Test 1 was conducted by use of a reaction vessel with a volume of 1 L. The reaction vessel comprises a conduit and a pump for taking out the liquid in the reaction vessel and for taking back the liquid into the reaction vessel.

Putting 0.75 L (0.80 kg) of a fluorine-containing hydrochloric acid (density: 1.07 g/cm$^3$) having a hydrogen chloride concentration of 13% by weight and a fluorine concentration of 2100 ppm and 0.10 L (0.076 kg) of a hexamethyl disiloxane (HMDS, density: 0.764 g/cm$^3$) into the reaction vessel, they were separated into two phases. The tip of the conduit was placed in the organic phase containing HMDS on the upper side. The inner diameter of the tip of the conduit was 4.37 mm. The liquid inside the reaction vessel was mixed by taking back a liquid, which was taken out from the lower part of the reaction vessel, into the reaction vessel via the conduit and the pump. The flow rate of the liquid ejected from the conduit was set to 20 L/min. The Liquid in the reaction vessel was made into uniformly mixed state without phase separation. During the mixing, the liquid in the reaction vessel was sampled over time. Leaving the sampled liquid to stand, the liquid was phase-separated quickly. The fluorine concentration in the aqueous phase on the lower side was determined by a fluorine ion meter.
(Test 2)
Test 2 was conducted by use of the reaction vessel with a volume of 5 L. The reaction vessel comprises a conduit and a pump for taking out the liquid in the reaction vessel and for taking back the liquid into the reaction vessel. The inner diameter of the tip of the conduit was 4.37 mm. Test 2 was carried out by the same procedure as that in Test 1 except that 3.75 L (4.01 kg) of a fluorine-containing hydrochloric acid having a hydrogen chloride concentration of 13% by weight and a fluorine concentration of 2518 ppm and 0.51 L the (0.39 kg) of a hexamethyl disiloxane (HMDS) were used and that the flow rate of a liquid ejected from the conduit was set to 1.43 L/min. During the mixing, the liquid in the reaction vessel was made into uniformly mixed state without phase separation.
(Test 3)
Test 3 was conducted by use of a reaction vessel with a volume of 13 L. The reaction vessel comprises a conduit and a pump for taking out the liquid in the reaction vessel and for taking back the liquid into the reaction vessel. An ejection member was attached to the tip of the conduit. The ejection member has a nozzle and a diffuser attached to the tip of the nozzle, and the diffuser has a plurality of openings on the side of the tip of the nozzle. The inner diameter of the tip of the nozzle was 1.5 mm.

Putting 9.4 L (10.05 kg) of a fluorine-containing hydrochloric acid having a hydrogen chloride concentration of 13% by weight and a fluorine concentration of 1829 ppm and 1.5 L (1.15 kg) of a hexamethyl disiloxane (HMDS) into the reaction vessel, they were separated into two phases. The ejection member was placed such that the tip of the nozzle and the openings of the diffuser were located in the organic phase on the upper side. The liquid inside the reaction vessel was mixed by taking back a liquid, which was taken out from the lower part of the reaction vessel, into the reaction vessel via the conduit and the pump. The flow rate of the liquid ejected from the tip of the nozzle was set to 3.3 L/min. The Liquid in the reaction vessel was made into uniformly mixed state without phase separation. During the mixing, the liquid in the reaction vessel was sampled over time. Leaving the sampled liquid to stand, the liquid was phase-separated quickly. The fluorine concentration in the aqueous phase on the lower side was determined by the fluorine ion meter. In addition, HCl concentration in the aqueous phase at the end of mixing was determined by a titration method.
(Test 4)
Test 4 was conducted by use of the same reaction vessel as that used in Test 3. The reaction vessel comprises a conduit and a pump for taking out the liquid in the reaction vessel and for taking back the liquid into the reaction vessel. An ejection member was attached to the tip of the conduit. The ejection member has a nozzle and a diffuser attached to the tip of the nozzle, and the diffuser has a plurality of openings on the side of the tip of the nozzle. The inner diameter of the tip of the nozzle was 1.5 mm. Test 4 was carried out by the same procedure as that in Test 3 except that 9.7 L (10.3 kg) of a fluorine-containing hydrochloric acid having a hydrogen chloride concentration of 13% by weight and a fluorine concentration of 1829 ppm and 1.51 L the (1.15 kg) of a hexamethyl disiloxane (HMDS) were used and that the flow rate of a liquid ejected from the tip of the nozzle was set to 1.4 L/min. The liquid in the reaction vessel is made into uniformly mixed state without phase separation.

fluorine-containing aqueous solution and HMDS can be facilitated when the flow rate of the ejection flow is the same. Further, it has been found from the results of Tests 3 and 4 that HCl concentration was not substantially changed before and after the reaction step when the fluorine-containing hydrochloric acid was processed by the method of the present invention. That is, it has been found that the fluorine ion is reacted with HMDS selectively to remove the fluorine ion selectively even in a case where chlorine ion is present in large amount compared to the fluorine ion.

TABLE 1

|  | Test 1 | Test 2 | Test 3 | Test 4 |
| --- | --- | --- | --- | --- |
| Fluorine-containing hydrochloric acid/HMDS (ratio by weight) | 10/1 | 10/1 | 10/1 | 10/1 |
| HCl concentration (wt %) | 13 | 13 | 13 | 13 |

| Mixing time (min) | Fluorine concentration (ppm) | Fluorine concentration (ppm) | Fluorine concentration (ppm) | Fluorine concentration (ppm) |
| --- | --- | --- | --- | --- |
| 0 | 2100 | 2518 | 1829 | 1829 |
| 3 | — | — | 981 | 1544 |
| 5 | — | — | 536 | 1456 |
| 10 | 4 | 1950 | 14 | 1210 |
| 20 | 4 | 1925 | 10 | 907 |
| 30 | — | 1923 | — | — |
| 40 | 4 | 1582 | 12 | 358 |
| 60 | — | 1801 | — | — |
| 90 | — | 1744 | — | — |
| Volume of HMDS (L) | 0.10 | 0.51 | 1.5 | 1.5 |
| Volume of fluorine-containing hydrochloric acid (L) | 0.75 | 3.75 | 9.4 | 9.7 |
| Total volume (L) | 0.85 | 4.26 | 10.9 | 11.2 |
| Ejection flow rate (L/min) | 20 | 1.43 | 3.3 | 1.4 |
| Frequency of replacement (1/min) | 23.3 | 0.34 | 0.30 | 0.13 |
| Linear velocity (m/min) | 1336 | 95.6 | 1867 | 792 |
| HCl concentration at end of mixing (wt %) | — | — | 13 | 13 |

Figure 8:
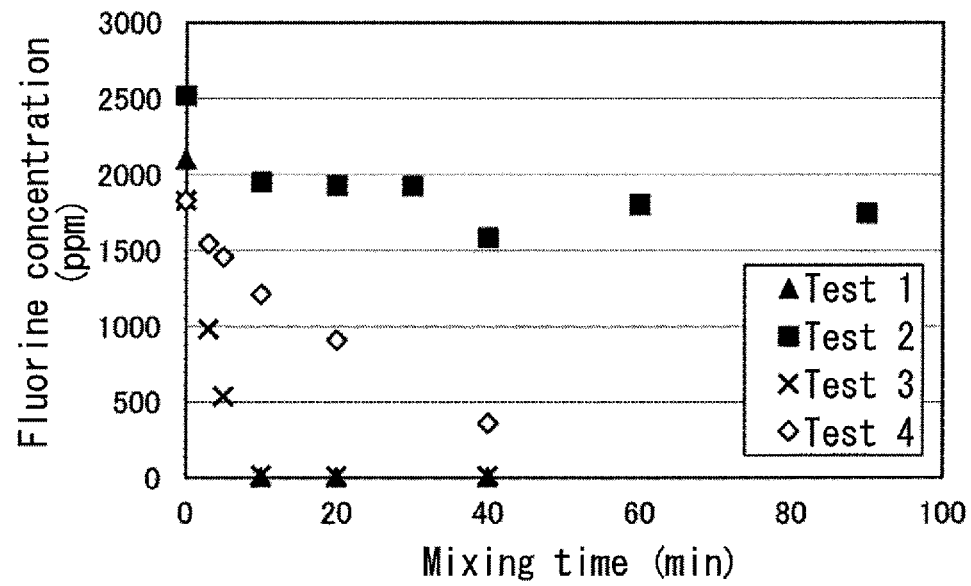
FIG. 8 is a graph showing results of Tests 1 to 4 in Examples.

The results of Tests 1 to 4 are shown in Table 1 and FIG. 8. In addition, the calculation results of the linear velocities of the ejection flows at the tip of the conduit for Tests 1 and 2, and the calculation results of the linear velocities of the ejection flows at the tip of the nozzle of the ejection member for Tests 3 and 4 are shown in Table 1. It can be seen from Table 1 that the decrease rate of the fluorine concentration was increased as the linear velocity was larger. This is considered to be caused by the following matters: the mixing in the vertical direction was carried out more effectively as the linear velocity was higher, and the progress of the reaction of the above formula (I) was facilitated. It can be seen from the comparison of the results of Tests 1 and 2 with the results of Tests 3 and 3 that larger linear velocity could be achieved with lower flow rate by use of the ejection member provided with the nozzle. Therefore, it is considered that the mixing in the vertical direction can be carried out more effectively by use of the ejection member provided with the nozzle so that the reaction of the fluorine in the (Test 5)

Putting 0.014 L (0.015 kg) of a fluorine-containing hydrochloric acid having a hydrogen chloride concentration of 14% by weight and a fluorine concentration of 2158 ppm and 0.020 L the (0.015 kg) of hexamethyl disiloxane (HMDS) into a reaction vessel with a volume of 250 mL, they were separated into two phases. The liquid in the reaction vessel was mixed by stirring with a stirrer chip. Number of revolution of the stirrer chip was set to 1000 rpm. During the stirring, the liquid in the reaction vessel remained phase-separated. During the stirring, the aqueous phase on the lower side was sampled over time, and the fluorine concentration in the aqueous phase was determined by the fluorine ion meter.

Figure 9:
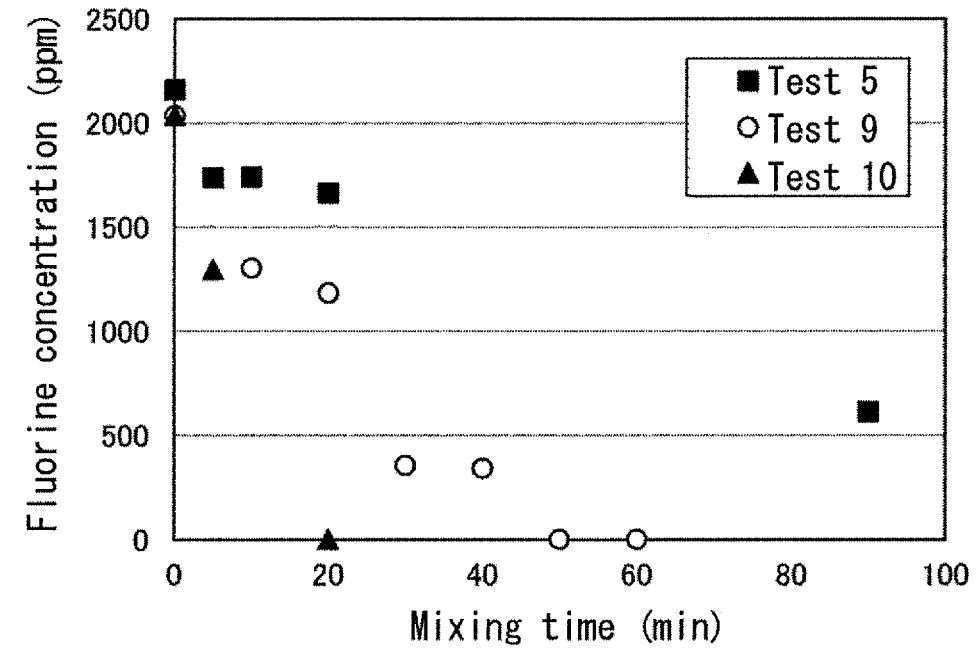
FIG. 9 is a graph showing results of Tests 5, 9 and 10 in Examples.

The result of Test 5 is shown in FIG. 9. The fluorine concentration after 20 minutes from the start of the mixing was 1739 ppm, the fluorine concentration after 90 minutes was 613 ppm, and the fluorine concentration of 100 ppm or less could not be achieved.

Example 2. Mixing by Ultrasonic Wave

In Tests 6 to 8 described below, the reaction step was carried out by use of an ultrasonic generator 91 comprising a tubular reactor 9 and a vibrator 92 shown in FIG. 6. Inner diameter of the tubular reactor 9 was ⅛ inches (0.32 cm) and the overall length of the tubular reactor 9 was 20 m. This tubular reactor 9 was placed in the ultrasonic generator 91 and filled with pure water as a medium. The temperature in the tubular reactor 9 was set to 35° C. The output power of the ultrasonic wave generator 91 was set to 400 W, and the frequency of the vibrator 92 was set to 38 kHz.

(Test 6)

100.91 g of a fluorine-containing hydrochloric acid having a hydrogen chloride concentration of 14% by weight and a fluorine concentration of 2136 ppm and 16.98 g of HMDS were continuously fed to the tubular reactor 9 by means of the pump 61. The residence time (i.e., irradiation time of ultrasonic wave) was set to 13.6 minutes. Leaving the liquid taken out from the tubular reactor 9 to stand, it was separated into two phases immediately. The fluorine concentration in the aqueous phase on the lower side was determined by the fluorine ion meter.

(Test 7)

Test 7 was carried out by the same procedure as that in Test 6 except that the used amount of the fluorine-containing hydrochloric acid was 292.38 g, the used amount of HMDS was 18.00 g and the residence time was 5.45 minutes.

(Test 8)

Test 8 was carried out by the same procedure as that in Test 6 except that the used amount of the fluorine-containing hydrochloric acid was 384.15 g, the used amount of HMDS was 97.85 g and the residence time was 1.63 minutes.

Figure 10:
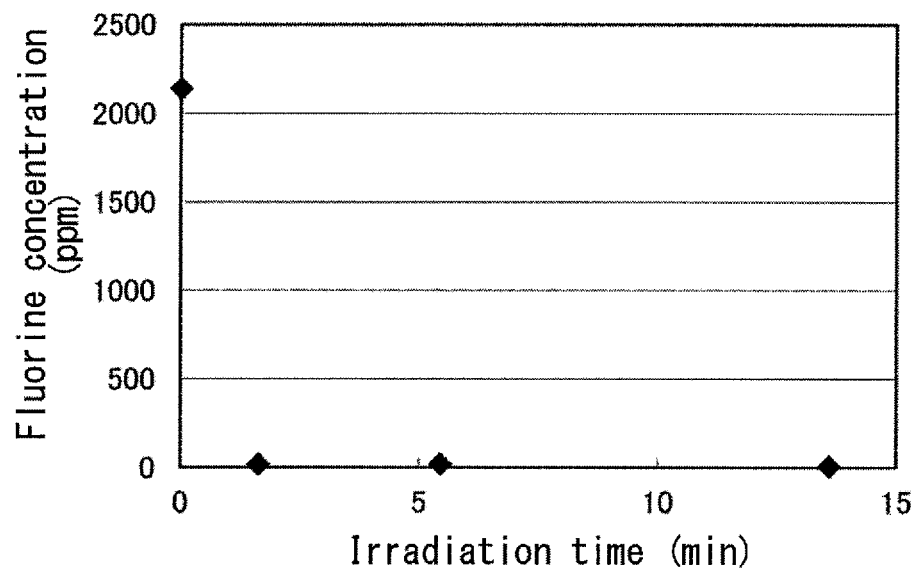
FIG. 10 is a graph showing results of Tests 6 to 8 in Examples.

The results of Tests 6 to 8 were shown in Table 2 and FIG. 10. In FIG. 10, the vertical axis represents the fluorine concentration in the aqueous phase and the horizontal axis represents the residence time (i.e., irradiation time). The fluorine concentration in the aqueous phase at a residence time of 1.63 minutes was 16.9 ppm, and the fluorine concentration of 100 ppm or less can be achieved at the residence time of 1.63 minutes or more.

TABLE 2

| | Fluorine-containing hydrochloric acid (g) | HMDS (g) | Residence time (min) | Fluorine concentration (ppm) |
|---|---|---|---|---|
| Test 6 | 100.91 | 16.98 | 13.6 | 4.2 |
| Test 7 | 292.38 | 18.00 | 5.45 | 16.6 |
| Test 8 | 384.15 | 97.85 | 1.63 | 16.9 |

Example 3. Temperature Dependence of Reaction Time

The following Tests 9 and 10 were carried out to examine the temperature dependence of the time required for the reaction in the reaction step.

(Test 9)

Test 9 was carried out by the same procedure as that in Test 5 except that the temperature during the mixing was set to 50° C. During the mixing, the liquid in the reaction vessel remained phase-separated.

(Test 10)

Test 10 was carried out by the same procedure as that in Test 5 except that the temperature during the mixing was set to 80° C. During the mixing, the liquid in the reaction vessel remained phase-separated.

The results of Tests 5, 9 and 10 are shown in FIG. 9. It can be seen from FIG. 9 that the time required for the reaction is decreased as the temperature in the reaction step is higher. When the reaction temperature was 80° C. (Test 10), the fluorine concentration of 100 ppm or less in the aqueous phase was achieved after 20 minutes from the start of the mixing. In contrast, when the reaction temperature was room temperature (Test 5), the fluorine concentration of 100 ppm or less in the aqueous phase could not be achieved even after 90 minutes from the start of the mixing.

Example 4. Hydrogen Chloride Concentration Dependence of Reaction Time

The following Tests 11 to 14 were carried out to examine the hydrogen chloride concentration dependence of the time required for the reaction in the reaction step.

(Test 11)

Test 11 was carried out by the same procedure as that in Test 5 except that a fluorine-containing hydrochloric acid having a hydrogen chloride concentration of 0% by weight and a fluorine concentration of 1976 ppm was used.

(Test 12)

Test 12 was carried out by the same procedure as that in Test 5 except that a fluorine-containing hydrochloric acid having a hydrogen chloride concentration of 20.3% by weight and a fluorine concentration of 2100 ppm was used.

(Test 13)

Test 13 was carried out by the same procedure as that in Test 5 except that a fluorine-containing hydrochloric acid having a hydrogen chloride concentration of 24.6% by weight and a fluorine concentration of 2000 ppm was used.

(Test 14)

Test 14 was carried out by the same procedure as that in Test 5 except that a fluorine-containing hydrochloric acid having a hydrogen chloride concentration of 28.7% by weight and a fluorine concentration of 1800 ppm was used.

Figure 11:
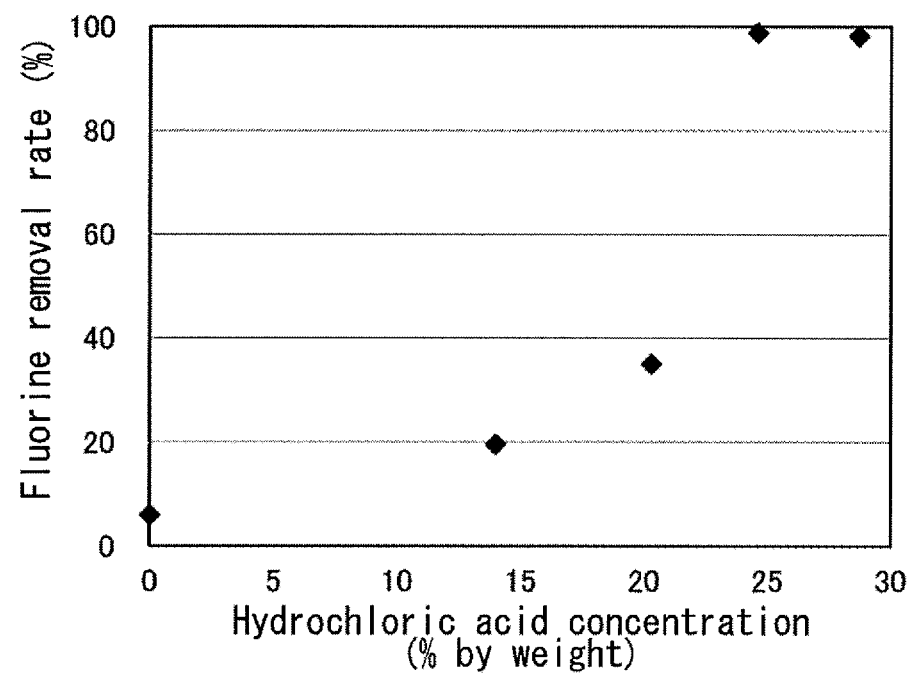
FIG. 11 is a graph showing results of Tests 5 and 11 to 14 in Examples.

The results of Tests 5 and 11 to 14 are shown in FIG. 11. In FIG. 11, vertical axis represents a removal rate of fluorine after 5 minutes from the start of the mixing, and horizontal axis represents the hydrogen chloride concentration in the fluorine-containing hydrochloric acid. The removal rate of fluorine is represented by the following equation.

(Removal rate of fluorine) %={(weight of fluorine ion and fluorine present in fluorine-containing hydrochloric acid before start of mixing)−(weight of fluorine ion and fluorine remaining in aqueous phase after mixing)}/(weight of fluorine ion and fluorine present in fluorine-containing hydrochloric acid before start of mixing)×100

As shown in FIG. 11, the removal rate of fluorine was increased as the hydrogen chloride concentration in the fluorine-containing hydrochloric acid was higher. From this, it can be seen that the time required for the reaction step can be shortened as the hydrogen chloride concentration in the fluorine-containing hydrochloric acid is higher.

Example 5. First Separation Step (Test 15)

Figure 12:
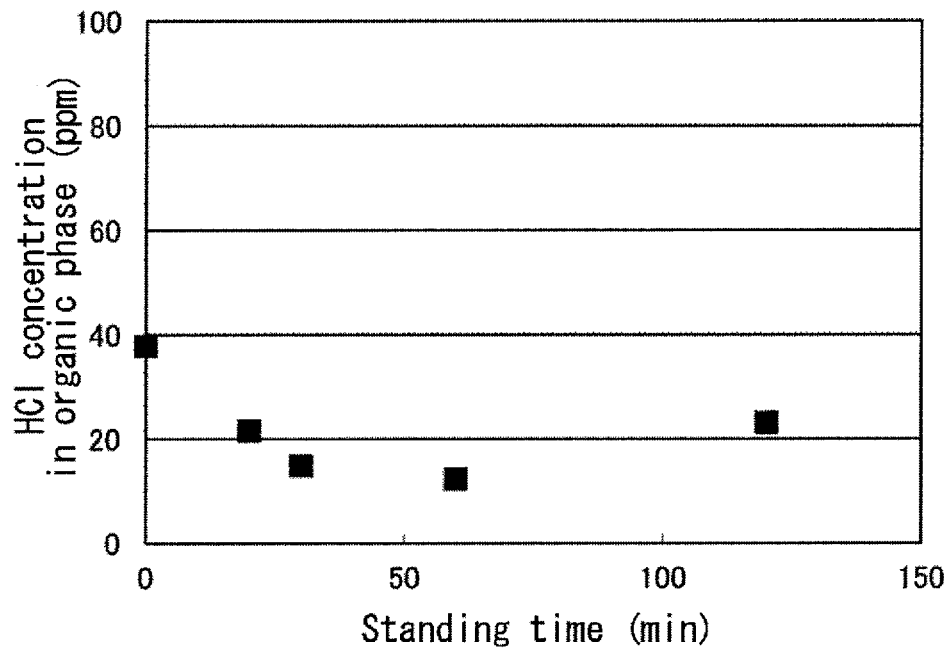
FIG. 12 is a graph showing a result of Test 15 in Examples.
Figure 13:
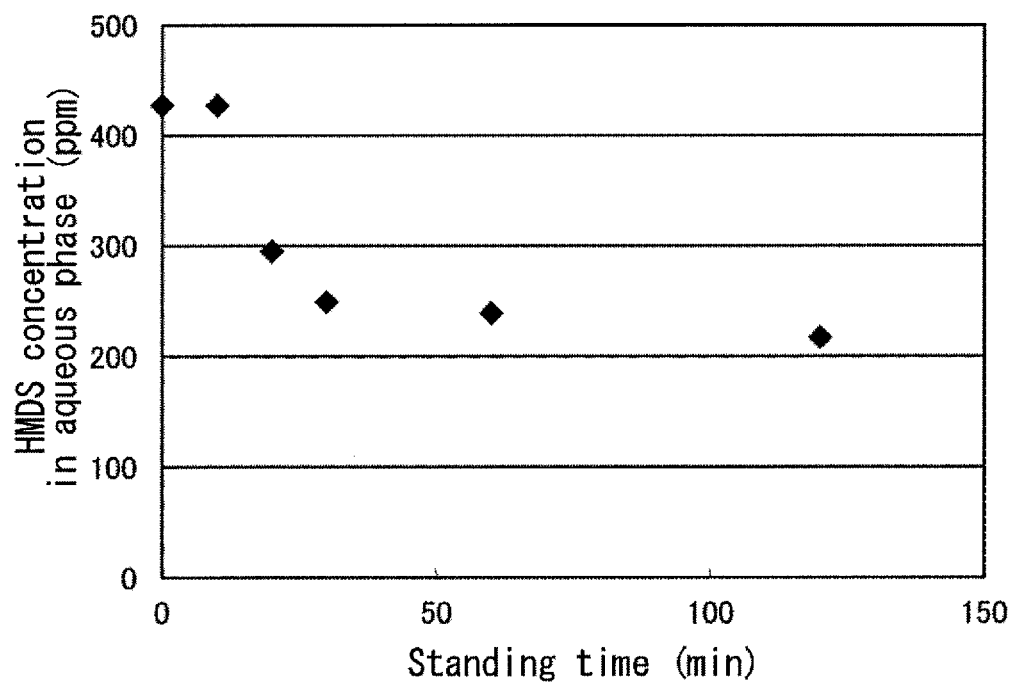
FIG. 13 is a graph showing a result of Test 15 in Examples.

The reaction step was carried out by same procedure as that in Test 3. The mixing was stopped after 10 minutes from the start of the mixing. The fluorine concentration in the aqueous phase upon stopping the mixing was 14 ppm. The liquid in the reaction vessel was separated into two phases immediately after stopping the mixing. The liquid in the reaction vessel was left to stand, and the organic phase on the upper side and the aqueous phase on the lower side were sampled over time. The HMDS concentration and the trimethylfluorosilane (TMFS) concentration in the sampled aqueous phase were determined by gas chromatography, and the hydrogen chloride concentration in the sampled organic phase was determined by ion chromatography. The organic phase and the aqueous phase were collected separately after 120 minutes after stopping the mixing. The result is shown in Table 3 and FIGS. 12 and 13. In FIGS. 12 and 13, "standing time" means a time from a point of stopping the mixing. The TMFS concentration in the aqueous phase was 10 ppm or less at the point of stopping the mixing. Thus, it can be seen that the fluorine compound in the aqueous phase was removed by the reaction step. The hydrogen chloride concentration in the organic phase was reduced to 20 ppm or less within 30 minutes. In addition, the HMDS concentration in the aqueous phase was reduced to 300 ppm or less within 30 minutes. It has been found from the results described above that the first separation step could be completed in about 30 minutes from stopping the mixing.

TABLE 3

| Standing time (min) | Aqueous phase | | Organic phase |
| --- | --- | --- | --- |
| | HMDS concentration (ppm) | TMFS concentration (ppm) | HCl concentration (ppm) |
| 0 | 427 | 7 | 37.8 |
| 10 | 427 | 5 | — |
| 20 | 295 | 5 | 21.6 |
| 30 | 249 | 8 | 14.9 |
| 60 | 239 | 7 | 12.3 |
| 120 | 217 | 8 | 23.1 |

Example 6. Regeneration Step (Test 16)

The TMFS concentration in the organic phase recovered in Test 15 was determined by gas chromatography to be 6.2% by weight. 1.764 L (1.348 kg) of this organic phase containing TMFS and HMDS and 2.794 L (2.934 kg) of 5% by weight sodium hydroxide (NaOH) aqueous solution as a basic aqueous solution were putted into a reaction vessel with a volume of 5 L. The reaction vessel comprises a conduit and a pump for taking out the liquid in the reaction vessel and for taking back the liquid into the reaction vessel, and an ejection member comprising a nozzle and a diffuser is attached to the tip of the conduit. The inner diameter of the tip of the nozzle was 1.5 mm. The molar ratio of NaOH present in the NaOH aqueous solution to the trimethylfluorosilane present in the organic phase was NaOH/TMFS=4.0.

Figure 14:
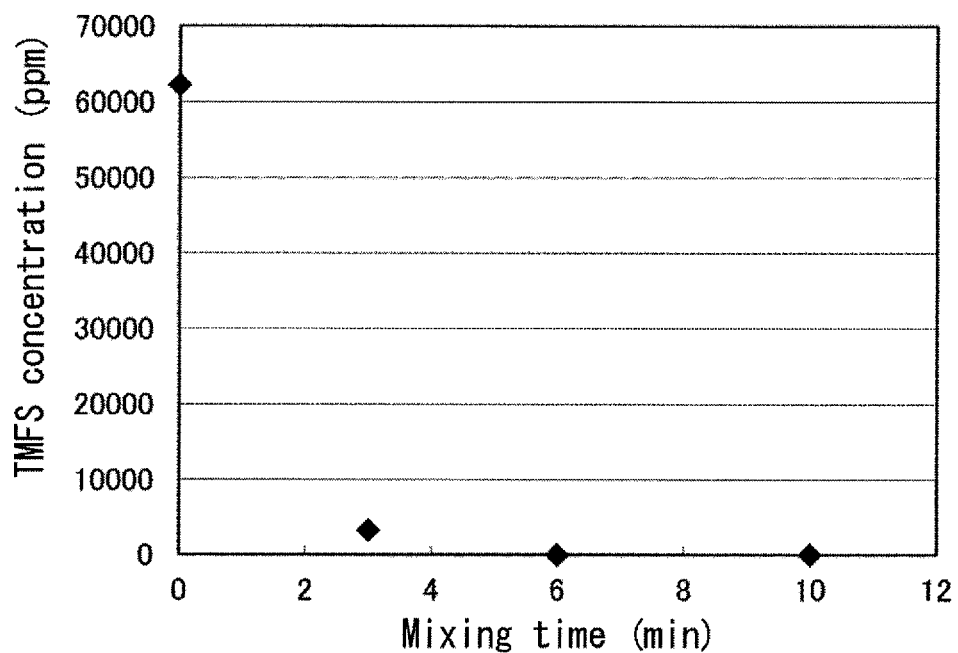
FIG. 14 is a graph showing a result of Test 16 in Examples.

The ejection member was placed so that the openings of the diffuser are located in the organic phase on the upper side. The liquid in the reaction vessel was mixed by taking back the liquid, which was taken out from the lower part of the reaction vessel, into the reaction vessel via the conduit and the pump. The flow rate of the liquid ejected from the tip of the nozzle was set to 1.4 L/min. The linear velocity of the ejection flow at the tip of the second nozzle 111 was 792 m/min. The liquid in the reaction vessel was made into uniformly mixed state without phase separation. During the mixing, the liquid in the reaction vessel was sampled over time. Leaving the sampled liquid to stand, it was phase-separated immediately. The TMFS concentration in the organic phase on the upper side was determined by gas chromatography. The results are shown in Table 4 and FIG. 14. The TMFS concentration in the organic phase became undetected (less than 0.1 ppm) after 6 minutes from the start of the mixing. It can be seen from this fact that almost all of TMFS was regenerated into HMDS within 6 minutes from the start of the mixing.

TABLE 4

| Mixing time (min) | Ejection flow rate (L/min) | TMFS concentration (ppm) |
| --- | --- | --- |
| 0 | 1.4 | 62220 |
| 3 | 1.4 | 3260 |
| 6 | 1.4 | <0.1 |
| 10 | 1.4 | <0.1 |

Example 7. Molar Ratio of Base in Regeneration Step

The following Tests 17 to 22 were carried out for examine a relation between the molar ratio of the base contained in the basic aqueous solution used in the regeneration step to TMFS contained in the organic phase obtained in the first separation step and the HMDS regeneration rate. Any of Tests 17 to 22 was carried out at room temperature.

(Test 17)

29.51 g of a HMDS solution having a TMFS concentration of 35328 ppm and 0.93 g of 5% by weight NaOH aqueous solution were putted into a screw tube and the screw tube was sealed. The molar ratio of NaOH to TMFS contained in the HMDS solution was 0.1. The mixing in this screw tube was carried out in a direction perpendicular to an interface between the organic phase and the aqueous phase, that is, in the vertical direction at about 200 to 250 rpm for 15 minutes. After completion of the mixing, leaving the screw tube to stand, the liquid inside the screw tube was phase-separated immediately. The organic phase on the upper side and the aqueous phase on the lower side were sampled, respectively. The TMFS concentration in the organic phase was determined by gas chromatography. The pH value of the aqueous phase was determined by a pH meter.

(Test 18)

Test 18 was carried out by the same procedure as that in Test 17 except that the amount of the HMDS solution was 30.01 g and the amount of the NaOH aqueous solution was 4.61 g. The molar ratio of NaOH to TMFS contained in the HMDS solution was 0.5. After completion of the test, pH in the aqueous phase and TMFS concentration in the organic phase were determined.

(Test 19)

Test 19 was carried out by the same procedure as that in Test 17 except that the amount of the HMDS solution was 29.98 g and the amount of the NaOH aqueous solution was 9.21 g. The molar ratio of NaOH to TMFS contained in the HMDS solution was 1.0. After completion of the test, pH in the aqueous phase and TMFS concentration in the organic phase were determined.

(Test 20)

Test 20 was carried out by the same procedure as that in Test 17 except that the amount of the HMDS solution was 30.00 g and the amount of the NaOH aqueous solution was 11.98 g. The molar ratio of NaOH to TMFS contained in the HMDS solution was 1.3. After completion of the test, pH in the aqueous phase and TMFS concentration in the organic phase were determined.

(Test 21)

Test 21 was carried out by the same procedure as that in Test 17 except that the amount of the HMDS solution was 19.96 g and the amount of the NaOH aqueous solution was 9.34 g. The molar ratio of NaOH to TMFS contained in the HMDS solution was 1.5. After completion of the test, pH in the aqueous phase and TMFS concentration in the organic phase were determined.

(Test 22)

Test 22 was carried out by the same procedure as that in Test 17 except that the amount of the HMDS solution was 20.01 g and the amount of the NaOH aqueous solution was 11.21 g. The molar ratio of NaOH to TMFS contained in the HMDS solution was 1.8. After completion of the test, pH in the aqueous phase and TMFS concentration in the organic phase were determined.

Figure 15:
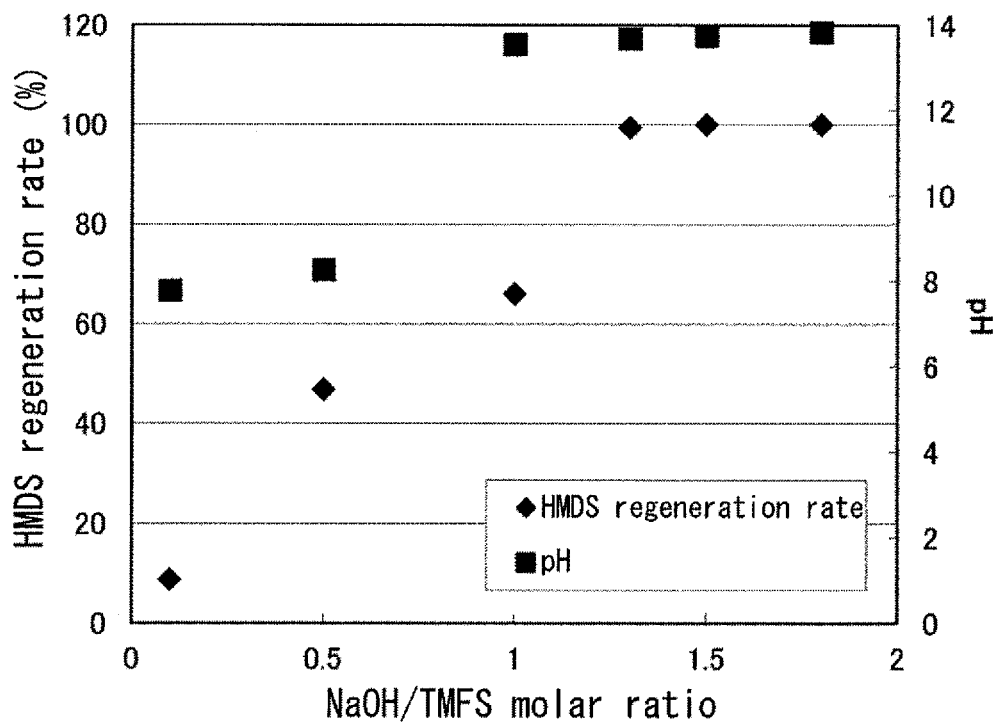
FIG. 15 is a graph showing results of Tests 17 to 22 in Examples.

The results of Tests 17 to 22 are shown in Table 5 and FIG. 15. In FIG. 15, main vertical axis on the left represents the regeneration rate of HMDS, second vertical axis represents pH of the aqueous phase, and the horizontal axis represents a molar ratio of NaOH contained in the NaOH aqueous solution to the trimethylfluorosilane contained in the HMDS solution. The regeneration rate of HMDS is represented by the following formula.

(HMDS regeneration rate) %={(weight of TMFS present in the HMDS solution before start of mixing)−(weight of TMFS remaining in organic phase after mixing)}/(weight of TMFS present in HMDS solution before start of mixing)×100

It can be seen from Table 5 and FIG. 15 that the HMDS regeneration rate of 99% or more could be achieved in a mixing time of 15 minutes when the molar ratio of NaOH to TMFS was 1.3 or more.

TABLE 5

|  | NaOH/TMFS molar ratio | TMFS concentration (ppm) | pH | HMDS regeneration rate (%) |
| --- | --- | --- | --- | --- |
| Test 17 | 0.1 | 32244 | 7.77 | 8.73 |
| Test 18 | 0.5 | 18791 | 8.26 | 46.81 |
| Test 19 | 1 | 12021 | 13.55 | 65.97 |
| Test 20 | 1.3 | 225 | 13.68 | 99.36 |
| Test 21 | 1.5 | <0.1 | 13.75 | 100 |
| Test 22 | 1.8 | <0.1 | 13.84 | 100 |

Example 8. Regeneration Step Using Static Mixer

In the following Tests 23 to 27, the regeneration step was carried out by use of a static mixer. Any of Tests 23 to 27 was carried out at room temperature by use of a static mixer having an inner diameter of 9.52 mm and an overall length of 180 mm.

(Test 23)

In Test 23, an organic phase containing TMFS and HMDS and 5% by weight NaOH aqueous solution were continuously fed a to a static mixer. The flow rate for feeding the organic phase was 1.179 L/min, the flow rate for feeding the NaOH aqueous solution was 0.166 L/min, and the flow velocity of the liquid (the sum of the organic phase and the NaOH aqueous solution) at the inlet of the static mixer was 0.315 m/s. The liquid was sampled over time at the outlet of the static mixer. Upon leaving the sampled liquid to stand, it was phase-separated immediately. The TMFS concentration in the organic phase on the upper side was determined by gas chromatography.

(Test 24)

Test 24 was carried out by the same procedure as that in Test 23 except that the flow rate for feeding the organic phase was 0.236 L/min, the flow rate for feeding the NaOH aqueous solution was 0.196 L/min and the flow velocity of the liquid (the sum of the organic phase and the NaOH aqueous solution) at the inlet of the static mixer was 0.101 m/s.

(Test 25)

Test 25 was carried out by the same procedure as that in Test 23 except that the flow rate for feeding the organic phase was 0.236 L/min, the flow rate for feeding the NaOH aqueous solution was 0.0646 L/min and the flow velocity of the liquid (the sum of the organic phase and the NaOH aqueous solution) at the inlet of the static mixer was 0.07 m/s.

(Test 26)

Test 26 was carried out by the same procedure as that in Test 23 except that the flow rate for feeding the organic phase was 0.236 L/min, the flow rate for feeding the NaOH aqueous solution was 0.238 L/min and the flow velocity of the liquid (the sum of the organic phase and the NaOH aqueous solution) at the inlet of the static mixer was 0.10 m/s.

(Test 27)

Test 27 was carried out by the same procedure as that in Test 23 except that the flow rate for feeding the organic phase was 1.179 L/min, the flow rate for feeding the NaOH aqueous solution was 0.238 L/min and the flow velocity of the liquid (the sum of the organic phase and the NaOH aqueous solution) at the inlet of the static mixer was 0.33 m/s.

Figure 16:
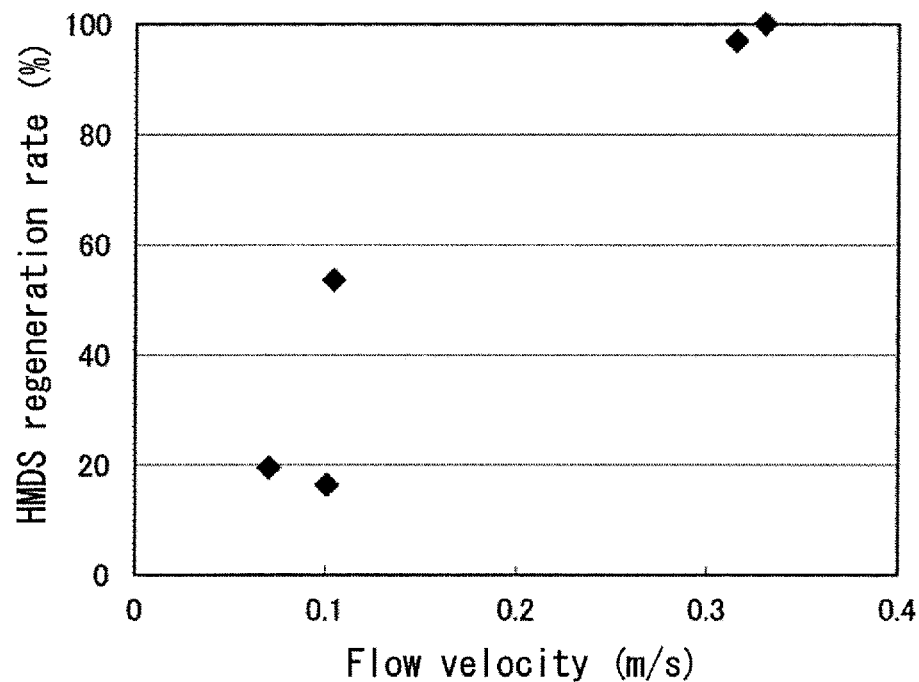
FIG. 16 is a graph showing results of Tests 23 to 27 in Examples.

The results of the Tests 23 to 27 are shown in Table 6 and FIG. 16. FIG. 16 plots a regeneration rate at the end of each test relative to a flow velocity. It can be seen that the regeneration rate of HMDS was increased as the flow velocity of the liquid at the inlet of the static mixer is higher, that is, as the Reynolds number (Re) is larger. In Tests 23 and 27 where the Reynolds number was about 2300 or more, that is, where the flow of the liquid in the static mixer was a turbulent flow, the HMDS regeneration rate of 95% or more could be achieved. This is considered to be because the miscibility of the organic phase with the NaOH aqueous solution was increased due to the flow of the liquid within the static mixer being turbulent flow.

TABLE 6

|  | Test 23 | Test 24 | Test 25 |
| --- | --- | --- | --- |
| Flow rate of organic phase (L/min) | 1.179 | 0.236 | 0.236 |

TABLE 6-continued

| | | | |
|---|---|---|---|
| Flow rate of NaOH aqueous solution (L/min) | 0.166 | 0.196 | 0.0646 |
| flow velocity (m/s) | 0.315 | 0.101 | 0.07 |
| Re | 2896 | 1146 | 665 |

| Mixing time (s) | TMFS concentration (ppm) | HMDS regeneration rate (%) | TMFS concentration (ppm) | HMDS regeneration rate (%) | TMFS concentration (ppm) | HMDS regeneration rate (%) |
|---|---|---|---|---|---|---|
| 0 | 85907 | — | 34867 | — | 72806 | — |
| 20 | 2355 | 97.3 | — | — | 56954 | 21.8 |
| 30 | — | — | 31160 | 10.6 | — | — |
| 40 | 2628 | 96.9 | 28530 | 18.2 | — | — |
| 50 | — | — | — | — | 56537 | 22.3 |
| 60 | 2600 | 97.0 | — | — | — | — |
| 70 | — | — | — | — | — | — |
| 80 | — | — | 29161 | 16.4 | — | — |
| 90 | — | — | — | — | 58604 | 19.5 |

| | Test 26 | Test 27 |
|---|---|---|
| Flow rate of organic phase (L/min) | 0.236 | 1.179 |
| Flow rate of NaOH aqueous solution (L/min) | 0.238 | 0.238 |
| flow velocity (m/s) | 0.10 | 0.33 |
| Re | 1194 | 3144 |

| Mixing time (s) | TMFS concentration (ppm) | HMDS regeneration rate (%) | TMFS concentration (ppm) | HMDS regeneration rate (%) |
|---|---|---|---|---|
| 0 | 183288 | — | 248142 | — |
| 20 | — | — | <0.1 | 100 |
| 30 | 58691 | 68.0 | — | — |
| 40 | — | — | <0.1 | 100 |
| 50 | — | — | — | — |
| 60 | 90962 | 50.4 | <0.1 | 100 |
| 70 | — | — | — | — |
| 80 | — | — | — | — |
| 90 | 85019 | 53.6 | — | — |

Example 9. Second Separation Step (Test 28)

Figure 17:
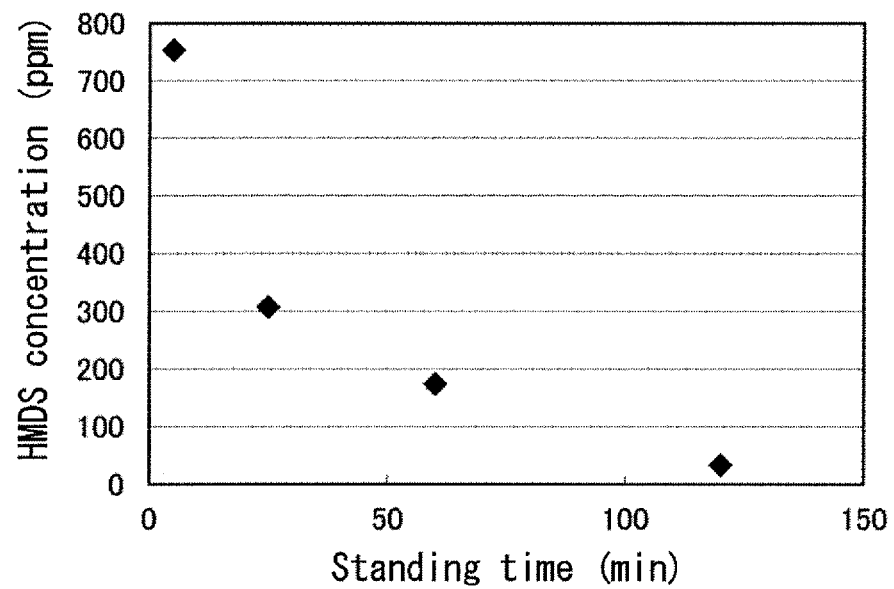
FIG. 17 is a graph showing a result of Test 28 in Examples.

A regeneration step was carried out by the same procedure as that in Test 16. The mixing was stopped after 10 minutes from the start of the mixing. TMFS concentration upon stopping the mixing was undetected (less than 0.1 ppm). The liquid in the reaction vessel was separated into two phases immediately after the stop of the mixing. After the mixing was stopped, the aqueous phase at the lower side was sampled over time. The HMDS concentration in the sampled aqueous phase was determined by gas chromatography. After 120 minutes after stopping the mixing, the organic phase and the aqueous phase were collected separately. The result is shown in Table 7 and FIG. 17. In FIG. 17, "standing time" means a time from a point of stopping the mixing. The HMDS concentration in the aqueous phase was decreased to approximately 300 ppm within 25 minutes. It has been found from this result that the second separation step could be completed in about 25 minutes from stopping the mixing.

TABLE 7

| Standing time (min) | HMDS concentration in aqueous phase (ppm) |
|---|---|
| 5 | 753 |
| 25 | 307 |
| 60 | 173 |
| 120 | 33 |

Example 10. Recycle of Regenerated Hexamethyl Disiloxane (Test 29)

Test 29 was carried out by the same procedure as that in Test 3 except that 1.5 L (1.13 kg) of an organic phase recovered in Test 28, that is, the regenerated HMDS and 9.3 L (9.95 kg) of a fluorine-containing aqueous solution having a hydrogen chloride concentration of 12.8% by weight and a fluorine concentration of 1829 ppm were used.

Figure 18:
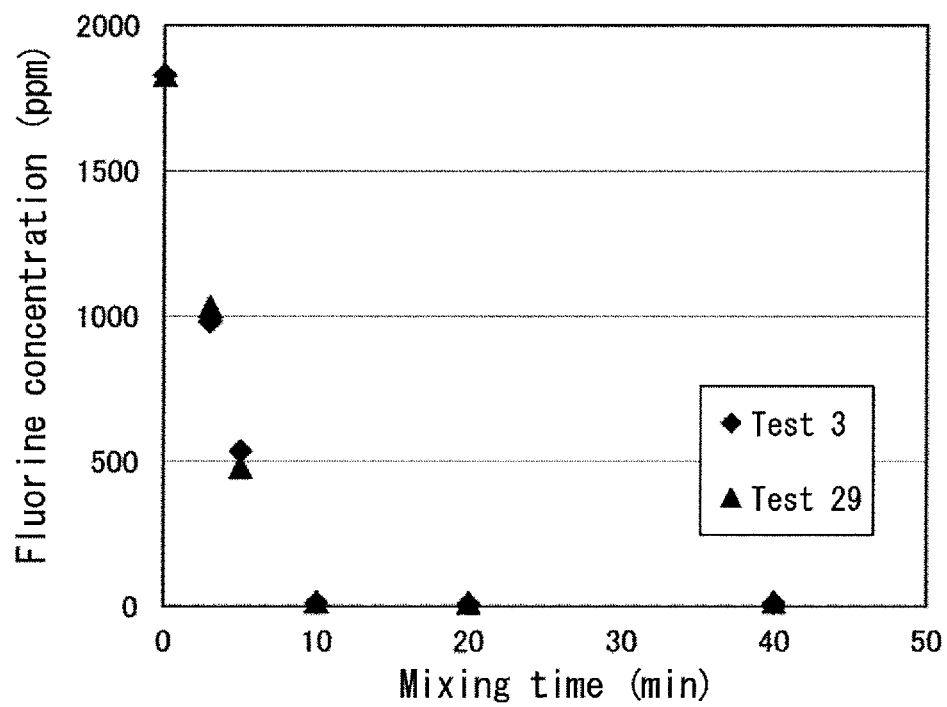
FIG. 18 is a graph showing results of Tests 3 and 29 in Examples.

The result of Test 29 is shown in Table 8 and FIG. 18. For comparison, the result of Test 3 using new HMDS is also shown in FIG. 18. It has been found from FIG. 18 that the fluorine in the fluorine-containing aqueous solution can be removed in a short time similarly to the case of using new HMDS even when the regenerated HMDS was used.

TABLE 8

|  | Test 29 |
|---|---|
| Fluorine-containing hydrochloric acid/HMDS (ratio in weight) | 10/1 |
| HCl concentration (wt %) | 13 |

| Mixing time (min) | Fluorine concentration (ppm) |
|---|---|
| 0 | 1829 |
| 3 | 1033 |
| 5 | 480 |
| 10 | 16 |
| 20 | 13 |
| 40 | 16 |
| Volume of HMDS (L) | 1.5 |
| Volume of fluorine-containing hydrochloric acid (L) | 9.3 |
| Total volume (L) | 10.8 |
| Ejection flow rate (L/min) | 3.3 |
| Frequency of replacement (1/min) | 0.30 |
| Linear velocity (m/min) | 1867 |

Example 11. Processing of Fluorine-Containing Hydrochloric Acid by Continuous Reaction (Test 30)

The reaction step, the first separation step, the regeneration step and the second separation step were carried out by use of the apparatus shown in FIG. 2. Each step was carried out continuously.

(Reaction Step)

The first reaction vessel 300 used in the reaction step has a volume of 5.3 L and comprises a conduit 6 and a pump 61 for taking out the liquid in the reaction vessel and for taking back the liquid into the reaction vessel. The first ejection member 100 is attached to the tip of the conduit 6. The first ejection member 100 comprises a first nozzle 1 and a first diffuser 2 attached to the tip of the nozzle 1, and the first diffuser 2 has a plurality of openings on the side of the tip of the first nozzle 1. The inner diameter of the tip of the first nozzle 1 was 1.5 mm.

Figure 19:
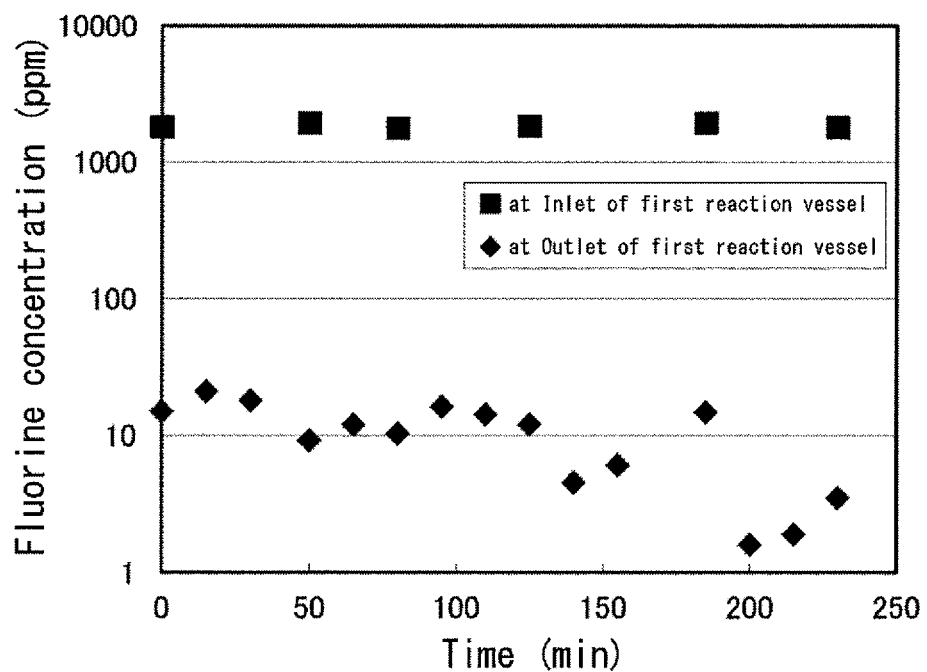
FIG. 19 is a graph showing a result of the reaction step in Test 30 in Examples.

3.83 kg (3.58 L) of a fluorine-containing hydrochloric acid having a hydrogen chloride concentration of 15.5% by weight and a fluorine concentration of about 1932 ppm and 0.383 kg (0.50 L) of HMDS were put into the first reaction vessel 300, and the reaction step was carried out in a batch-wise way. The liquid in the first reaction vessel 300 was mixed by taking back a liquid, which was taken out from the lower part of the first reaction vessel 300, into the first reaction vessel 300 via a conduit 6 and a pump 61. The flow rate of the liquid ejected from the tip of the first nozzle 1 was set to 2.4 L/min. The linear velocity of the ejection flow at the tip of the first nozzle 1 was 1358 m/min. The liquid in the first reaction vessel 300 were sampled over time. Leaving the sampled liquid to stand, the liquid was phase-separated immediately. The fluorine concentration in the aqueous phase on the lower side was determined by a fluorine ion meter. The fluorine concentrations after 15 minutes and 20 minutes from the start of the mixing were 21 ppm and 15 ppm, respectively. Thus, it has been found that sufficient residence time in the first reaction vessel 300 was about 15 minutes when the reaction step was carried out continuously. The batch-wise reaction step was completed after 20 minutes from the start of the mixing. The apparatus was set such that the liquid overflowing from the first reaction vessel 300 was fed to the first separation vessel 400, and the continuous reaction step was carried out by the following procedure. A fluorine-containing hydrochloric acid having a hydrogen chloride concentration of 15.6% by weight and a fluorine concentration of about 1770 to 1930 ppm and HMDS were continuously fed to the first reaction vessel 300, and overflowing liquid was fed to the subsequent first separation vessel 400. The flow rate of the hydrochloric acid was set to about 207 to 264 mL/min, the flow rate of HMDS was set to about 30 to 34 mL/min, and the residence time was set to about 13 to 17 minutes. The liquid in the first reaction vessel 300 was mixed by taking back a liquid, which was taken out from the lower part of the first reaction vessel 300, into the first reaction vessel 300 via the conduit 6 and the pump 61. The flow rate of the liquid ejected from the first tip of the nozzle 1 was set to 2.4 L/min. The linear velocity of the ejection flow at the tip of the first nozzle 1 was 1358 m/min. According to the monitoring of the temperature and the pressure in the first reaction vessel 300, temperature rise and pressure rise were not observed. The first reaction liquid was sampled over time at the outlet of the first reaction vessel 300. Leaving the sampled liquid to stand, it was phase-separated immediately. The fluorine concentration in the aqueous phase on the lower side was determined by a fluorine ion meter. Also, the fluorine-containing hydrochloric acid was sampled over time at the inlet of the first reaction vessel 300, and the fluorine concentration of the fluorine-containing hydrochloric acid was determined. The results are shown in Table 9 and FIG. 19. For the data described in Table 9 and FIG. 19, the point of starting the reaction step continuously is defined as a starting point (zero minute). It can be seen from FIG. 19 that the fluorine concentration in the aqueous phase was maintained to 100 ppm or less at the outlet of the first reaction vessel 300.

TABLE 9

| Time (min) | Feeding flow rate of fluorine-containing hydrochloric acid (mL/min) | Feeding flow rate of HMDS (mL/min) | residence time (min) | Ejection flow rate in reaction vessel (mL/min) | Linear velocity (m/min) | Fluorine concentration at inlet of reaction vessel (ppm) | Fluorine concentration at outlet of reaction vessel (ppm) |
|---|---|---|---|---|---|---|---|
| 0 | — | — | — | — | — | 1804 | 15 |
| 15 | — | — | — | — | — | — | 21 |

TABLE 9-continued

| Time (min) | Feeding flow rate of fluorine-containing hydrochloric acid (mL/min) | Feeding flow rate of HMDS (mL/min) | residence time (min) | Ejection flow rate in reaction vessel (mL/min) | Linear velocity (m/min) | Fluorine concentration at inlet of reaction vessel (ppm) | Fluorine concentration at outlet of reaction vessel (ppm) |
|---|---|---|---|---|---|---|---|
| 30 | — | — | — | — | — | — | 18 |
| 35 | 207.4 | 31.8 | 17.06 | 2400 | 1358 | — | — |
| 50 | — | — | — | — | — | 1934 | 9.2 |
| 65 | — | — | — | — | — | — | 12 |
| 80 | 264 | 34.0 | 13.69 | 2400 | 1358 | 1770 | 10.3 |
| 95 | — | — | — | — | — | — | 16.3 |
| 110 | — | — | — | — | — | — | 14.2 |
| 125 | 212.7 | 30.50 | 16.78 | 2400 | 1358 | 1830 | 12.1 |
| 140 | — | — | — | — | — | — | 4.5 |
| 155 | — | — | — | — | — | — | 6.1 |
| 185 | 231 | 33.5 | 15.43 | 2400 | 1358 | 1930 | 14.8 |
| 200 | — | — | — | — | — | — | 1.6 |
| 215 | — | — | — | — | — | — | 1.9 |
| 230 | 264 | 31.0 | 13.83 | 2400 | 1358 | 1792 | 3.5 |

(First Separation Step)

The first reaction liquid obtained in the first reaction vessel 300 was continuously fed to a first separation vessel 400 with a volume of 9.7 L. The first reaction liquid fed to the first separation vessel 400 was phase-separated immediately. The residence time in the first separation vessel 400 was set to from 27.0 to 33.6 minutes. According to the monitoring of the TMFS concentration in the organic phase on the upper side, the TMFS concentration was from 40694 to 66551 ppm. According to the monitoring of the HMDS concentration and the TMFS concentration in the aqueous phase on the lower side, the HMDS concentration was maintained to 400 ppm or less, and the TMFS concentration was maintained to 10 ppm or less. The aqueous phase was obtained as a purified aqueous solution at the lower part of the first separation vessel. Overflowing organic phase on the upper side containing TMFS and HMDS was fed to the subsequent regeneration step. The result is shown in Table 10.

TABLE 10

| | Organic phase | | Aqueous phase | | |
|---|---|---|---|---|---|
| Time (min) | TMFS concentration (ppm) | HCl concentration (ppm) | HMDS concentration (ppm) | TMFS concentration (ppm) | Residence time (min) |
| 0 | — | — | — | — | — |
| 15 | 49947 | 0.8 | 174 | <0.1 | — |
| 30 | 40694 | 2.8 | 215 | <0.1 | — |
| 35 | — | — | — | — | 33.6 |
| 50 | 61219 | 0.7 | 129 | <0.1 | — |
| 65 | 64770 | 4.0 | 367 | 10 | — |
| 80 | 66551 | 2.4 | 397 | 10 | 27.0 |
| 95 | 53493 | 3.6 | 1 | 3 | — |
| 110 | 54784 | 4.7 | 82 | 4 | — |
| 125 | 60848 | 0.4 | 54 | 4 | 33.1 |
| 140 | 66260 | — | 1 | 2 | — |
| 155 | 63717 | — | 10 | 3 | — |
| 185 | 52591 | — | 1 | 8 | 30.4 |
| 200 | — | — | — | — | — |
| 215 | — | — | 56 | — | — |
| 230 | — | 1.2 | 72 | — | 27.3 |

(Regeneration Step)

The second reaction vessel 500 used in the regeneration step has a volume of 5.4 L and comprises a conduit 6 and a pump 61 for taking out a liquid in the second reaction vessel and for taking back the liquid into the second reaction vessel. The second ejection member 101 is attached to the tip of the conduit 6. The second ejection member 101 comprises a second nozzle 111 and a second diffuser 211 attached to the tip of the second nozzle 111, and the second diffuser 211 has a plurality of openings on the side of the tip of the second nozzle 111. The inner diameter of the tip of the second nozzle 111 was 1.5 mm.

Figure 20:
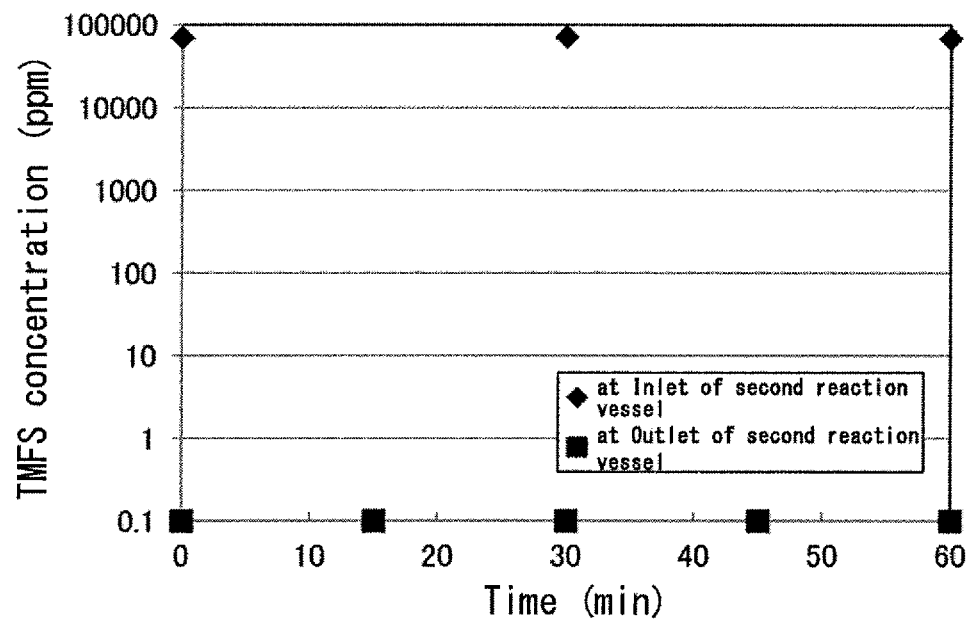
FIG. 20 is a graph showing a result of the regeneration step in Test 30 in Examples.

1.460 kg (1.911 L) of an organic phase containing TMFS and HMDS recovered in the first separation step and 2.375 kg the (2.262 L) of 5% by weight NaOH aqueous solution were put into the second reaction vessel 500, and the regeneration step was carried out in a batch-wise way. The liquid in the reaction vessel 500 was mixed by taking back a liquid, which was taken out from the lower part of the second reaction vessel 500, into the second reaction vessel 500 via a conduit 6 and a pump 61. The flow rate of the liquid ejected from the tip of the nozzle was set to 1.4 L/min. The linear velocity of the ejection flow at the tip of the second nozzle 111 was 792 m/min. The batch-wise regeneration step was completed after 10 minutes from the start of the mixing. The apparatus was set such that the liquid overflowing from the second reaction vessel 500 was fed to the second separation vessel 600, and the continuous regeneration step was carried out by the following procedure. The organic phase containing TMFS and HMDS recovered in the first separation step and 5% by weight NaOH aqueous solution were continuously fed to the second reaction vessel 500. The flow rate of HMDS solution was set to about 84.8 mL/min, the flow rate of the NaOH aqueous solution was set to 93.13 mL/min and the residence time was set to 22.93 minutes. The liquid in the reaction vessel 500 was mixed by taking back a liquid, which was taken out from the lower part of the second reaction vessel 500, into the second reaction vessel 500 via a conduit 6 and a pump 61. The flow rate of the liquid ejected from the tip of the nozzle was set to 1.4 L/min. The linear velocity of the ejection flow at the tip of the second nozzle 111 was 792 m/min. According to the monitoring of the temperature and the pressure in the second reaction vessel 500, temperature rise and pressure rise were not observed. The second reaction liquid was sampled over time at the outlet of the second reaction vessel 500. Leaving the sampled liquid to stand, it was phase-separated immediately. The TMFS concentration of the organic phase on the upper side was determined. Also, the organic phase was sampled over time at the inlet of the second reaction vessel 500, and the TMFS concentration in the organic phase was determined. The results are shown in Table 11 and FIG. 20. As shown in FIG. 20, the TMFS concentration in the organic phase was maintained to be undetected (less than 0.1 ppm) at the outlet of the second reaction vessel 500. This shows that TMFS present in the organic phase was regenerated into HMDS in the regeneration step.

TABLE 11

| Time (min) | Feeding flow rate of organic phase (mL/min) | Feeding flow rate of NaOH aqueous solution (mL/min) | Residence time (min) | TMFS concentration at inlet of reaction vessel (ppm) | TMFS concentration at outlet of reaction vessel (ppm) |
|---|---|---|---|---|---|
| 0 | — | — | — | 69700 | <0.1 |
| 15 | — | — | — | — | <0.1 |
| 30 | — | — | — | 71200 | <0.1 |
| 45 | — | — | — | — | <0.1 |
| 60 | 84.8 | 93.13 | 22.93 | 68700 | <0.1 |

(Second Separation Step)

Figure 21:
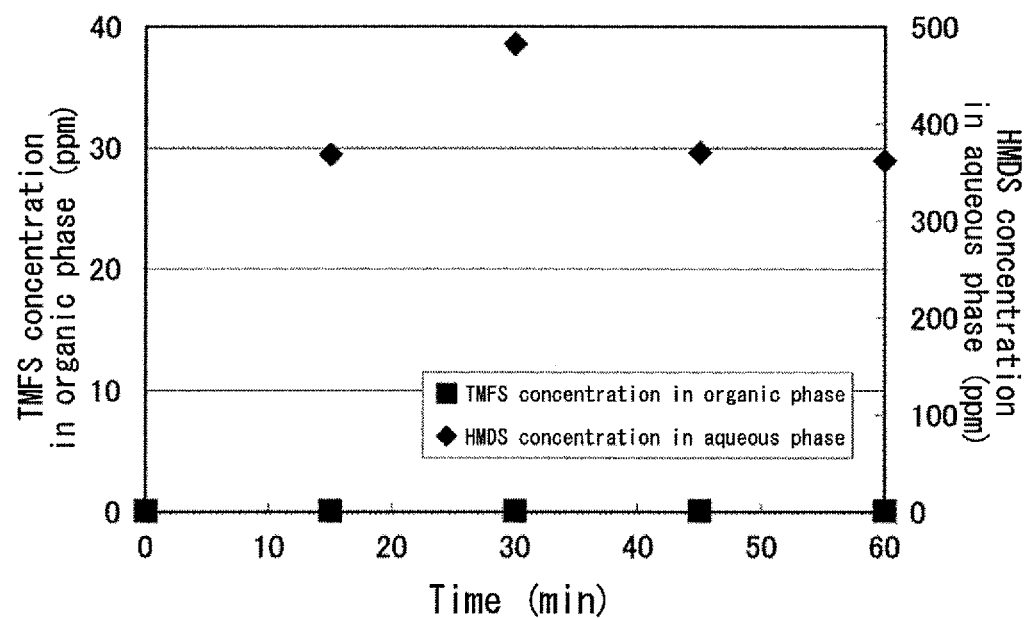
FIG. 21 is a graph showing a result of the second separation step in Test 30 in Examples.

The second reaction liquid obtained in the second reaction vessel 500 was continuously fed to a second separation vessel 600 with a volume of 5.1 L. The second reaction liquid fed to the second separation vessel 600 was phase-separated immediately. The residence time in the second separation vessel was set to 23.88 minutes. The result is shown in Table 12 and FIG. 21. According to monitoring of the TMFS concentration in the organic phase on the upper side, the TMFS concentration was maintained to be undetected (less than 0.1 ppm). According to the monitoring of the HMDS concentration and the TMFS concentration in the aqueous phase on the lower side, the HMDS concentration was maintained to 500 ppm or less, and the TMFS concentration was maintained to be undetected (less than 0.1 ppm). The aqueous phase on the lower side was obtained as a liquid containing fluoride salt at the lower part of the second separation vessel. Overflowing organic phase was recovered and fed back to the reaction step as a regenerated HMDS.

TABLE 12

| | Organic phase | Aqueous phase | | |
|---|---|---|---|---|
| Time (min) | TMFS concentration (ppm) | HMDS concentration (ppm) | TMFS concentration (ppm) | Residence time (min) |
| 15 | <0.1 | 368 | <0.1 | — |
| 30 | <0.1 | 482 | <0.1 | — |
| 45 | <0.1 | 370 | <0.1 | — |
| 60 | <0.1 | 362 | <0.1 | 23.88 |

As described above, the fluorine-containing hydrochloric acid could be processed continuously by carrying out the reaction step, the first separation step, the regeneration step and the second separation step in the continuous reactors, and the fluorine concentration of 100 ppm or less could be achieved.

INDUSTRIAL APPLICABILITY

The method for processing the fluorine-containing aqueous solution and the apparatus according to the present invention can process a large amount of waste liquid generated in the process for manufacturing the fluorine compound efficiently at low cost.

REFERENCE SIGNS LIST

100 first ejection member
101 second ejection member
1 first nozzle
111 second nozzle
13 tip of first nozzle
2 first diffuser
211 second diffuser
21 opening of first diffuser
22 end of first diffuser on the side of opening
23 tip of first diffuser
3 ejection flow from tip of first nozzle
31 Suction flow from the side
32 jet from tip of first diffuser
4 organic phase
41 organic component
5 aqueous phase
51 aqueous component
6 conduit
61 pump
7 disiloxane compound
8 fluorine-containing aqueous solution
9 first tubular reactor
91 ultrasonic generator
92 vibrator
10 first countercurrent reaction column
300 first reaction vessel
400 first separation vessel
500 second reaction vessel
600 second separation vessel

The invention claimed is:

1. A method for processing a fluorine-containing aqueous solution comprising:
    a reaction step for mixing in a vertical direction a fluorine-containing aqueous solution and a disiloxane compound represented by a general formula $R_aR_bR_cSiO\text{-}SiR_dR_eR_f$, wherein $R_a$, $R_b$, $R_c$, $R_d$, $R_e$ and $R_f$ are selected independently from each other from a group consisting of a phenyl group and an alkyl group comprising from 1 to 20 carbon atoms and hydrogen, wherein fluorine ions in the fluorine-containing aqueous solution are reacted with the disiloxane compound, so as to obtain a first reaction liquid comprising monofluorosilane compounds represented by general formulas $R_aR_bR_cSiF$ and $R_dR_eR_fSiF$,
    wherein mixing in the vertical direction in the reaction step is carried out by irradiating the fluorine-containing aqueous solution and the disiloxane compound with an ultrasonic wave.

2. The method according to claim 1, wherein the fluorine-containing aqueous solution is an acidic aqueous solution.

3. The method according to claim 2, wherein the fluorine-containing aqueous solution is a fluorine-containing hydrochloric acid.

4. The method according to claim 2, wherein the fluorine-containing aqueous solution has an acid concentration of 10% by weight or more.

5. The method according to claim 1, wherein the reaction step is conducted at a temperature of 50° C. or more.

6. The method according to claim 1, wherein the disiloxane compound is hexamethyl disiloxane.

7. The method according to claim 1, the method further comprising a first separation step for phase-separating the first reaction liquid obtained in the reaction step into an organic phase comprising the disiloxane compound and the monofluorosilane compound and an aqueous phase substantially free of the disiloxane compound and the monofluorosilane compound to obtain the aqueous phase as a purified aqueous solution with reduced fluorine concentration compared to the fluorine-containing aqueous solution.

8. The method according to claim 7, the method further comprising a regeneration step for mixing the organic phase obtained in the first separation step with a basic aqueous solution, thereby reacting the monofluorosilane compound contained in the organic phase with a base contained in the basic aqueous solution to obtain a second reaction liquid comprising a disiloxane compound and a fluoride salt.

9. The method according to claim 8, wherein the regeneration step is carried out by mixing the organic phase obtained in the first separation step and the basic aqueous solution in a vertical direction in a second reaction vessel, and wherein mixing in the vertical direction in the regeneration step is carried out by ejecting a liquid taken out from the second reaction vessel from a second ejection member comprising a second nozzle in the vertical direction in a liquid in the second reaction vessel.

10. The method according to claim 8, wherein mixing in the vertical direction in the regeneration step is carried out by ejecting a liquid taken out from a lower part of a second reaction vessel from a second ejection member comprising a second nozzle in a vertically downward direction in an upper part of a liquid in the second reaction vessel.

11. The method according to claim 10, wherein assuming that a total volume of an organic component contained in the liquid in the second reaction vessel is located on a total volume of an aqueous component contained in the liquid in the second reaction vessel and determining a virtual interface between the total volume of the organic component and the total volume of the aqueous component, the second ejection member is arranged such that a tip of the second nozzle is located in the organic component.

12. The method according to claim 11, wherein mixing in the vertical direction in the regeneration step is carried out by ejecting a liquid taken out from a lower part of the aqueous component from the second ejection member in a vertically downward direction.

13. The method according to claim 9, wherein mixing in the vertical direction in the regeneration step is carried out by ejecting a liquid taken out from an upper part of a second reaction vessel from a second ejection member comprising a second nozzle in a vertically upward direction in a lower part of the liquid in the second reaction vessel.

14. The method according to claim 13, wherein assuming that a total volume of an organic component contained in the liquid in the second reaction vessel is located on a total volume of an aqueous component contained in the liquid in the second reaction vessel and determining a virtual interface between the total volume of the organic component and the total volume of the aqueous component, the second ejection member is arranged such that a tip of the second nozzle is located in the aqueous component.

15. The method according to claim 14, wherein mixing in the vertical direction in the regeneration step is carried out by ejecting a liquid taken out from an upper part of the organic component from the second ejection member in the vertically upward direction.

16. The method according to claim 9, wherein the second ejection member further comprises a second diffuser attached to a tip of the second nozzle, and wherein the second diffuser has one or more openings on the side of the tip of the second nozzle.

17. The method according to claim 9, wherein a linear velocity of the ejection flow at the tip of the second nozzle is not less than 500 m/min and not more than 2000 m/min.

18. The method according to claim 9, wherein mixing in the vertical direction in the regeneration step is carried out by irradiating the organic phase obtained in the first separation step and the basic aqueous solution with an ultrasonic wave.

19. The method according to claim 8, wherein a molar ratio of the base contained in the basic aqueous solution used in the regeneration step to the monofluorosilane compound contained in the organic phase obtained in the first separation step is 1.3 or more.

20. The method according to claim 8, the method further comprising a second separation step for phase-separating the second reaction liquid obtained in the regeneration step into an organic phase comprising the disiloxane compound and substantially free of the fluoride salt and an aqueous phase comprising the fluoride salt and substantially free of the disiloxane compound,
wherein the organic phase obtained in the second separation step is recycled as the disiloxane compound in the reaction step.

21. A method for processing a fluorine-containing aqueous solution comprising:
a reaction step for mixing in a vertical direction a fluorine-containing aqueous solution and a disiloxane compound represented by a general formula $R_aR_bR_cSiO\text{-}SiR_dR_eR_f$, wherein $R_a$, $R_b$, $R_c$, $R_d$, $R_e$ and $R_f$ are selected independently from each other from a group consisting of a phenyl group and an alkyl group comprising from 1 to 20 carbon atoms and hydrogen, wherein fluorine ions in the fluorine-containing aqueous solution are reacted with the disiloxane compound, so as to obtain a first reaction liquid comprising monofluorosilane compounds represented by general formulas $R_aR_bR_cSiF$ and $R_dR_eR_fSiF$,
a first separation step for phase-separating the first reaction liquid obtained in the reaction step into an organic phase comprising the disiloxane compound and the monofluorosilane compound and an aqueous phase substantially free of the disiloxane compound and the monofluorosilane compound to obtain the aqueous phase as a purified aqueous solution with reduced fluorine concentration compared to the fluorine-containing aqueous solution, and
a regeneration step for mixing the organic phase obtained in the first separation step with a basic aqueous solution, thereby reacting the monofluorosilane compound contained in the organic phase with a base contained in the basic aqueous solution to obtain a second reaction liquid comprising a disiloxane compound and a fluoride salt,
wherein mixing in the regeneration step is in a vertical direction and is carried out by irradiating the organic phase obtained in the first separation step and the basic aqueous solution with an ultrasonic wave.

22. The method according to claim 21, wherein the reaction step is carried out in a first reaction vessel, and wherein mixing in the vertical direction in the reaction step is carried out by ejecting a liquid taken out from the first reaction vessel from a first ejection member comprising a first nozzle in the vertical direction in a liquid in the first reaction vessel.

23. The method according to claim 22, wherein the first ejection member further comprises a first diffuser attached to the tip of the first nozzle, and wherein the first diffuser has one or more openings on the side of the tip of the first nozzle.

24. The method according to claim 22, wherein a linear velocity of an ejection flow at the tip of the first nozzle is not less than 500 m/min and not more than 2000 m/min.

25. The method according to claim 21, wherein mixing in the vertical direction in the reaction step is carried out by ejecting a liquid taken out from a lower part of a first reaction vessel from a first ejection member comprising a first nozzle in a vertically downward direction in an upper part of a liquid in the first reaction vessel.

26. The method according to claim 25, wherein assuming that a total volume of an organic component contained in the liquid in the first reaction vessel is located on a total volume of an aqueous component contained in the liquid in the first reaction vessel and determining a virtual interface between the total volume of the organic component and the total volume of the aqueous component, the first ejection member is arranged such that a tip of the first nozzle is located in the organic component.

27. The method according to claim 26, wherein mixing in the vertical direction in the reaction step is carried out by ejecting a liquid taken out from a lower part of the aqueous component from the first ejection member in the vertically downward direction.

28. The method according to claim 21, wherein mixing in the vertical direction in the reaction step is carried out by ejecting a liquid taken out from an upper part of a first reaction vessel from a first ejection member comprising a first nozzle in a vertically upward direction in a lower part of the liquid in the first reaction vessel.

29. The method according to claim 28, wherein assuming that a total volume of an organic component contained in the liquid in the first reaction vessel is located on a total volume of an aqueous component contained in the liquid in the first reaction vessel and determining a virtual interface between the total volume of the organic component and the total volume of the aqueous component, the first ejection member is arranged such that a tip of the first nozzle is located in the aqueous component.

30. The method according to claim 29, wherein mixing in the vertical direction in the reaction step is carried out by ejecting a liquid taken out from an upper part of the organic component from the first ejection member in the vertically upward direction.

31. The method according to claim 21, wherein the fluorine-containing aqueous solution is an acidic aqueous solution.

32. The method according to claim 31, wherein the fluorine-containing aqueous solution is a fluorine-containing hydrochloric acid.

33. The method according to claim 31, wherein the fluorine-containing aqueous solution has an acid concentration of 10% by weight or more.

34. The method according to claim 21, wherein the reaction step is conducted at a temperature of 50° C. or more.

35. The method according to claim 21, wherein the disiloxane compound is hexamethyl disiloxane.

36. The method according to claim 21, wherein a molar ratio of the base contained in the basic aqueous solution used in the regeneration step to the monofluorosilane compound contained in the organic phase obtained in the first separation step is 1.3 or more.

37. The method according to claim 21, the method further comprising a second separation step for phase-separating the second reaction liquid obtained in the regeneration step into an organic phase comprising the disiloxane compound and substantially free of the fluoride salt and an aqueous phase comprising the fluoride salt and substantially free of the disiloxane compound,
wherein the organic phase obtained in the second separation step is recycled as the disiloxane compound in the reaction step.

38. A method for processing a fluorine-containing aqueous solution comprising:
a reaction step for mixing in a vertical direction a fluorine-containing aqueous solution and a disiloxane compound represented by a general formula $R_aR_bR_cSiO$-$SiR_dR_eR_f$, wherein $R_a$, $R_b$, $R_c$, $R_d$, $R_e$ and $R_f$ are selected independently from each other from a group consisting of a phenyl group and an alkyl group comprising from 1 to 20 carbon atoms and hydrogen, wherein fluorine ions in the fluorine-containing aqueous solution are reacted with the disiloxane compound, so as to obtain a first reaction liquid comprising monofluorosilane compounds represented by general formulas $R_aR_bR_cSiF$ and $R_dR_eR_fSiF$,
wherein the reaction step is carried out in a first reaction vessel, and wherein mixing in the vertical direction in the reaction step is carried out by ejecting a liquid taken out from the first reaction vessel from a first ejection member comprising a first nozzle in the vertical direction in a liquid in the first reaction vessel.

39. The method according to claim 38, wherein mixing in the vertical direction in the reaction step is carried out by ejecting a liquid taken out from a lower part of a first reaction vessel from a first ejection member comprising a first nozzle in a vertically downward direction in an upper part of a liquid in the first reaction vessel.

40. The method according to claim 39, wherein assuming that a total volume of an organic component contained in the liquid in the first reaction vessel is located on a total volume of an aqueous component contained in the liquid in the first reaction vessel and determining a virtual interface between the total volume of the organic component and the total volume of the aqueous component, the first ejection member is arranged such that a tip of the first nozzle is located in the organic component.

41. The method according to claim 40, wherein mixing in the vertical direction in the reaction step is carried out by ejecting a liquid taken out from a lower part of the aqueous component from the first ejection member in the vertically downward direction.

42. The method according to claim 38, wherein mixing in the vertical direction in the reaction step is carried out by ejecting a liquid taken out from an upper part of a first reaction vessel from a first ejection member comprising a first nozzle in a vertically upward direction in a lower part of the liquid in the first reaction vessel.

43. The method according to claim 42, wherein assuming that a total volume of an organic component contained in the liquid in the first reaction vessel is located on a total volume of an aqueous component contained in the liquid in the first reaction vessel and determining a virtual interface between the total volume of the organic component and the total volume of the aqueous component, the first ejection member is arranged such that a tip of the first nozzle is located in the aqueous component.

44. The method according to claim 43, wherein mixing in the vertical direction in the reaction step is carried out by ejecting a liquid taken out from an upper part of the organic component from the first ejection member in the vertically upward direction.

45. The method according to claim 38, wherein the first ejection member further comprises a first diffuser attached to the tip of the first nozzle, and wherein the first diffuser has one or more openings on the side of the tip of the first nozzle.

46. The method according to claim 38, wherein a linear velocity of an ejection flow at the tip of the first nozzle is not less than 500 m/min and not more than 2000 m/min.

47. The method according to claim 38, wherein the fluorine-containing aqueous solution is an acidic aqueous solution.

48. The method according to claim 47, wherein the fluorine-containing aqueous solution is a fluorine-containing hydrochloric acid.

49. The method according to claim 47, wherein the fluorine-containing aqueous solution has an acid concentration of 10% by weight or more.

50. The method according to claim 38, wherein the reaction step is conducted at a temperature of 50° C. or more.

51. The method according to claim 38, wherein the disiloxane compound is hexamethyl disiloxane.

52. The method according to claim 38, the method further comprising a first separation step for phase-separating the first reaction liquid obtained in the reaction step into an organic phase comprising the disiloxane compound and the monofluorosilane compound and an aqueous phase substantially free of the disiloxane compound and the monofluorosilane compound to obtain the aqueous phase as a purified aqueous solution with reduced fluorine concentration compared to the fluorine-containing aqueous solution.

53. The method according to claim 52, the method further comprising a regeneration step for mixing the organic phase obtained in the first separation step with a basic aqueous solution, thereby reacting the monofluorosilane compound contained in the organic phase with a base contained in the basic aqueous solution to obtain a second reaction liquid comprising a disiloxane compound and a fluoride salt.

54. The method according to claim 53, wherein the regeneration step is carried out by mixing the organic phase obtained in the first separation step and the basic aqueous solution in a vertical direction in a second reaction vessel, and wherein mixing in the vertical direction in the regeneration step is carried out by ejecting a liquid taken out from the second reaction vessel from a second ejection member comprising a second nozzle in the vertical direction in a liquid in the second reaction vessel.

55. The method according to claim 54, wherein mixing in the vertical direction in the regeneration step is carried out by ejecting a liquid taken out from a lower part of a second reaction vessel from a second ejection member comprising a second nozzle in a vertically downward direction in an upper part of a liquid in the second reaction vessel.

56. The method according to claim 55, wherein assuming that a total volume of an organic component contained in the liquid in the second reaction vessel is located on a total volume of an aqueous component contained in the liquid in the second reaction vessel and determining a virtual interface between the total volume of the organic component and the total volume of the aqueous component, the second ejection member is arranged such that a tip of the second nozzle is located in the organic component.

57. The method according to claim 56, wherein mixing in the vertical direction in the regeneration step is carried out by ejecting a liquid taken out from a lower part of the aqueous component from the second ejection member in a vertically downward direction.

58. The method according to claim 54, wherein mixing in the vertical direction in the regeneration step is carried out by ejecting a liquid taken out from an upper part of a second reaction vessel from a second ejection member comprising a second nozzle in a vertically upward direction in a lower part of the liquid in the second reaction vessel.

59. The method according to claim 58, wherein assuming that a total volume of an organic component contained in the liquid in the second reaction vessel is located on a total volume of an aqueous component contained in the liquid in the second reaction vessel and determining a virtual interface between the total volume of the organic component and the total volume of the aqueous component, the second ejection member is arranged such that a tip of the second nozzle is located in the aqueous component.

60. The method according to claim 59, wherein mixing in the vertical direction in the regeneration step is carried out by ejecting a liquid taken out from an upper part of the organic component from the second ejection member in the vertically upward direction.

61. The method according to claim 54, wherein the second ejection member further comprises a second diffuser attached to a tip of the second nozzle, and wherein the second diffuser has one or more openings on the side of the tip of the second nozzle.

62. The method according to claim 54, wherein a linear velocity of the ejection flow at the tip of the second nozzle is not less than 500 m/min and not more than 2000 m/min.

63. The method according to claim 53, wherein a molar ratio of the base contained in the basic aqueous solution used in the regeneration step to the monofluorosilane compound contained in the organic phase obtained in the first separation step is 1.3 or more.

64. The method according to claim 53, the method further comprising a second separation step for phase-separating the second reaction liquid obtained in the regeneration step into an organic phase comprising the disiloxane compound and substantially free of the fluoride salt and an aqueous phase comprising the fluoride salt and substantially free of the disiloxane compound,
wherein the organic phase obtained in the second separation step is recycled as the disiloxane compound in the reaction step.

65. A method for processing a fluorine-containing aqueous solution comprising:
a reaction step for mixing in a vertical direction a fluorine-containing aqueous solution and a disiloxane compound represented by a general formula $R_aR_bR_cSiO$-$SiR_dR_eR_f$, wherein $R_a$, $R_b$, $R_c$, $R_d$, $R_e$ and $R_f$ are selected independently from each other from a group consisting of a phenyl group and an alkyl group comprising from 1 to 20 carbon atoms and hydrogen, wherein fluorine ions in the fluorine-containing aqueous solution are reacted with the disiloxane compound, so as to obtain a first reaction liquid comprising monofluorosilane compounds represented by general formulas $R_aR_bR_cSiF$ and $R_dR_eR_fSiF$,
a first separation step for phase-separating the first reaction liquid obtained in the reaction step into an organic phase comprising the disiloxane compound and the monofluorosilane compound and an aqueous phase substantially free of the disiloxane compound and the monofluorosilane compound to obtain the aqueous phase as a purified aqueous solution with reduced fluorine concentration compared to the fluorine-containing aqueous solution, and a regeneration step for mixing the organic phase obtained in the first separation step with a basic aqueous solution, thereby reacting the monofluorosilane compound contained in the organic phase with a base contained in the basic aqueous solution to obtain a second reaction liquid comprising a disiloxane compound and a fluoride salt, wherein the regeneration step is carried out by mixing the organic phase obtained in the first separation step and the basic aqueous solution in a vertical direction in a second reaction vessel, and wherein mixing in the vertical direction in the regeneration step is carried out by ejecting a liquid taken out from the second reaction vessel from a second ejection member comprising a second nozzle in the vertical direction in a liquid in the second reaction vessel.

66. The method according to claim 65, wherein mixing in the vertical direction in the regeneration step is carried out by ejecting a liquid taken out from a lower part of a second reaction vessel from a second ejection member comprising a second nozzle in a vertically downward direction in an upper part of a liquid in the second reaction vessel.

67. The method according to claim 66, wherein assuming that a total volume of an organic component contained in the liquid in the second reaction vessel is located on a total volume of an aqueous component contained in the liquid in the second reaction vessel and determining a virtual interface between the total volume of the organic component and the total volume of the aqueous component, the second ejection member is arranged such that a tip of the second nozzle is located in the organic component.

68. The method according to claim 67, wherein mixing in the vertical direction in the regeneration step is carried out by ejecting a liquid taken out from a lower part of the aqueous component from the second ejection member in a vertically downward direction.

69. The method according to claim 65, wherein mixing in the vertical direction in the regeneration step is carried out by ejecting a liquid taken out from an upper part of a second reaction vessel from a second ejection member comprising a second nozzle in a vertically upward direction in a lower part of the liquid in the second reaction vessel.

70. The method according to claim 69, wherein assuming that a total volume of an organic component contained in the liquid in the second reaction vessel is located on a total volume of an aqueous component contained in the liquid in the second reaction vessel and determining a virtual interface between the total volume of the organic component and the total volume of the aqueous component, the second ejection member is arranged such that a tip of the second nozzle is located in the aqueous component.

71. The method according to claim 70, wherein mixing in the vertical direction in the regeneration step is carried out by ejecting a liquid taken out from an upper part of the organic component from the second ejection member in the vertically upward direction.

72. The method according to claim 65, wherein the second ejection member further comprises a second diffuser attached to a tip of the second nozzle, and wherein the second diffuser has one or more openings on the side of the tip of the second nozzle.

73. The method according to claim 65, wherein a linear velocity of the ejection flow at the tip of the second nozzle is not less than 500 m/min and not more than 2000 m/min.

74. The method according to claim 65, wherein a molar ratio of the base contained in the basic aqueous solution used in the regeneration step to the monofluorosilane compound contained in the organic phase obtained in the first separation step is 1.3 or more.

75. The method according to claim 65, the method further comprising a second separation step for phase-separating the second reaction liquid obtained in the regeneration step into an organic phase comprising the disiloxane compound and substantially free of the fluoride salt and an aqueous phase comprising the fluoride salt and substantially free of the disiloxane compound, wherein the organic phase obtained in the second separation step is recycled as the disiloxane compound in the reaction step.

\* \* \* \* \*